`US009409900B2`

(12) United States Patent
Kang et al.

(10) Patent No.: US 9,409,900 B2
(45) Date of Patent: Aug. 9, 2016

(54) COMPOUND FOR INCREASING KINASE ACTIVE AND APPLICATION THEREOF

(75) Inventors: Xinshan Kang, Beijing (CN); Wei Long, Beijing (CN); Cunbo Ma, Beijing (CN); Yanping Wang, Beijing (CN); Xiaoyan Shen, Beijing (CN); Yunyan Hu, Beijing (CN); Fenlai Tan, Beijing (CN); Yinxiang Wang, Beijing (CN)

(73) Assignees: FUJIAN HAIXI PHARMACEUTICALS, INC., Fuzhou, Fujian (CN); BETTA PHARMACUETICALS CO., LTD., Hangzhou, Zhejiang (CN); Xinshan Kang, Beijing (CN)

( * ) Notice: Subject to any disclaimer, the term of this patent is extended or adjusted under 35 U.S.C. 154(b) by 38 days.

(21) Appl. No.: 13/884,470

(22) PCT Filed: Nov. 9, 2011

(86) PCT No.: PCT/CN2011/082004
§ 371 (c)(1),
(2), (4) Date: May 9, 2013

(87) PCT Pub. No.: WO2012/062210
PCT Pub. Date: May 18, 2012

(65) Prior Publication Data
US 2013/0225587 A1       Aug. 29, 2013

(30) Foreign Application Priority Data

Nov. 9, 2010   (CN) .......................... 2010 1 0535640

(51) Int. Cl.
| | |
|---|---|
| *C07D 417/12* | (2006.01) |
| *C07D 233/88* | (2006.01) |
| *C07D 405/14* | (2006.01) |
| *C07D 417/14* | (2006.01) |
| *C07D 213/74* | (2006.01) |
| *C07D 213/80* | (2006.01) |
| *C07D 213/803* | (2006.01) |
| *C07D 241/20* | (2006.01) |
| *C07D 277/42* | (2006.01) |
| *C07D 285/08* | (2006.01) |
| *C07D 401/12* | (2006.01) |
| *C07D 403/12* | (2006.01) |
| *C07D 405/04* | (2006.01) |
| *C07D 405/12* | (2006.01) |
| *C07D 401/14* | (2006.01) |

(52) U.S. Cl.
CPC ............ *C07D 417/14* (2013.01); *C07D 213/74* (2013.01); *C07D 213/80* (2013.01); *C07D 213/803* (2013.01); *C07D 233/88* (2013.01); *C07D 241/20* (2013.01); *C07D 277/42* (2013.01); *C07D 285/08* (2013.01); *C07D 401/12* (2013.01); *C07D 401/14* (2013.01);
*C07D 403/12* (2013.01); *C07D 405/04* (2013.01); *C07D 405/12* (2013.01); *C07D 405/14* (2013.01); *C07D 417/12* (2013.01)

(58) Field of Classification Search
USPC ......................................................... 514/237
See application file for complete search history.

(56) References Cited

U.S. PATENT DOCUMENTS

| | | | |
|---|---|---|---|
| 4,771,062 A | 9/1988 | Raddatz et al. | |
| 2003/0040535 A1 | 2/2003 | Aspnes et al. | |
| 2003/0045535 A1 * | 3/2003 | Morris et al. | 514/264.11 |
| 2003/0186995 A1 * | 10/2003 | Kath et al. | 514/260.1 |
| 2004/0010031 A1 | 1/2004 | Coghlan et al. | |
| 2005/0020648 A1 * | 1/2005 | Bley et al. | 514/370 |
| 2010/0204208 A1 * | 8/2010 | Singh et al. | 514/217.04 |

FOREIGN PATENT DOCUMENTS

| | | | | |
|---|---|---|---|---|
| DE | 36 32 042 A1 | 9/1987 | | |
| WO | WO 01/74771 A1 | 10/2001 | | |
| WO | WO 03/026666 A1 | 4/2003 | | |
| WO | WO 2003/026666 A1 * | 4/2003 | ............ | A61K 31/506 |
| WO | WO 2009/042618 A1 * | 4/2009 | ............ | A01N 43/36 |
| WO | WO 2010/090875 A1 | 8/2010 | | |

OTHER PUBLICATIONS

Supplementary European Search Report for Application No. EP 11 83 9459 dated Jul. 29, 2014 by Christian Hass.
Examination Report for Application No. 11839459.2-1501/2638036 PCT/CN2011082004 dated Aug. 6, 2014.
International Search Report for PCT/CN2011/082004 mailed by the State Intellectual Property Office, the P.R. China on Feb. 23, 2012.

* cited by examiner

*Primary Examiner* — Jeffrey S Lundgren
*Assistant Examiner* — Zenab Olabowale
(74) *Attorney, Agent, or Firm* — RatnerPrestia

(57) ABSTRACT

The compound of Formula (I), pharmaceutically acceptable salts thereof, solvates thereof, chelates thereof, non-covalent complexes thereof or produgs of compounds mentioned above or the mixture of any form above mentioned are provided. The use of the compounds in manufacturing a medicament for the treatment and/or prevention of diabetes, obesity and related disorders.

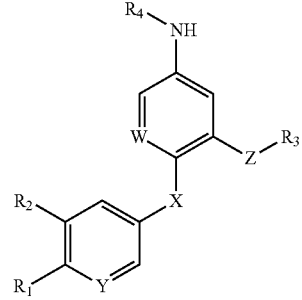

Formula (I)

24 Claims, 1 Drawing Sheet

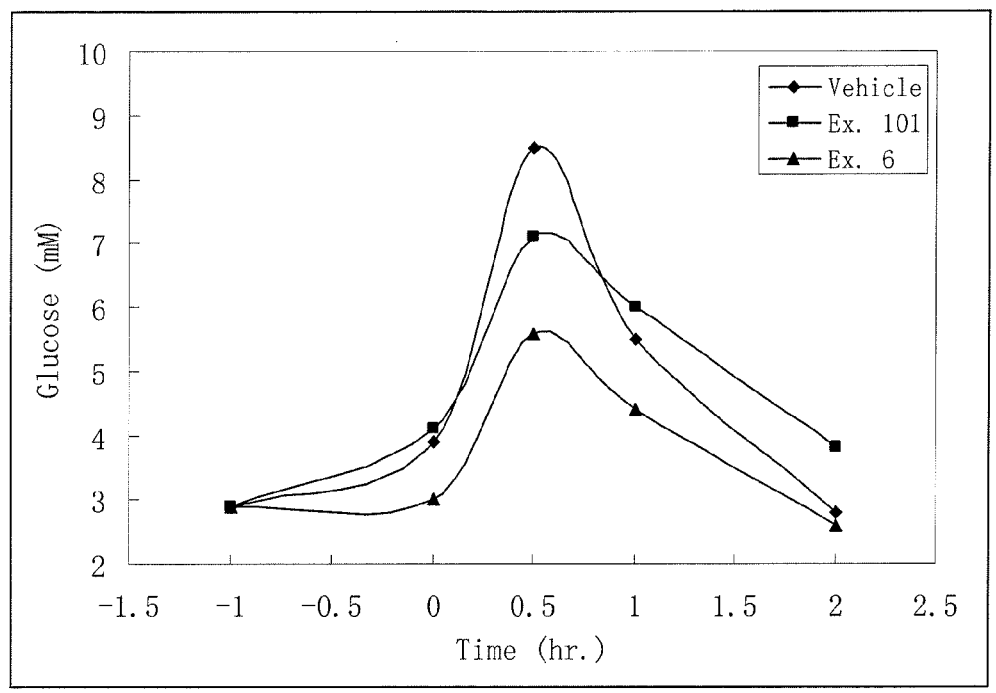

COMPOUND FOR INCREASING KINASE ACTIVE AND APPLICATION THEREOF

CROSS-REFERENCE TO RELATED APPLICATIONS

This application is a U.S. National Phase Application of PCT International Application PCT/CN2011/082004, filed Nov. 9, 2011, which claims priority to Chinese Application No. 201010535640.4, filed Nov. 9, 2010, the contents of each of which are incorporated herein by reference in their entireties for all purposes.

FIELD OF THE INVENTION

The present invention relates to compounds for increasing glucokinase activities and their use in manufacturing a medicament.

BACKGROUND OF THE INVENTION

Glucokinase (GK) is one (hexokinase IV) of four mammal hexokinases. Hexokinases is a first-stage enzyme in glycolysis and catalyzes a reaction from glucose to glucose hexaphosphate. In its expression, glucokinase is limited essentially in liver and pancreas beta cells, and it controls the rate limiting step of glucose metabolism in these cells. Thereby playing an important role in systemic saccharometabolism. Glucokinase in liver and that in pancreas beta cells differ from each other in point of the N-terminal 15-amino acid sequence owing to the difference in splicing there between, but they are the same in point of the enzymatic property. The enzymatic activity of the other three hexokinases (I, II, III) than glucokinase is saturated at a glucose concentration of at most 1 mM, but Km glucokinase to glucose is 8 mM and near to a physiological blood-glucose level. Thereof, in accordance with the blood-glucose level change from a normal blood-glucose level (5 nM) to an increased blood-glucose level after meals (10 to 15 mM), intracellular glucose metabolism is accelerated via glucokinase.

Since ten years ago, a hypothesis that glucokinase may act as a glucose sensor in pancreas beta cells and liver has been proposed [for example, see D. et al's "Computer modeling identified glucokinase as glucose sensor of pancreatic beta-cells", American Journal Physiology, V247 (3Pt2), 1984, p 527~536]. A result of recent glucokinase gene-manipulated mice has clarified that glucokinase actually plays an important role in systemic glucose homeostasis. Mice in which the glucokinase gene was disrupted die soon after their birth, but on the other hand, normal or diabetic mice in which glucokinase wad excessively expressed have a lowered blood-glucose level. With the increase in glucose concentration therein, the reacting of pancreas beta cells and that of liver cells are both toward the reduction in a blood-glucose level, though differing from each other. Pancreas beta cells come to secrete more insulin, and liver takes up sugar to store it as glycogen therein and simultaneously reduces sugar release.

To that effect, the change in the enzymatic activity of gulcokinase plays an important role in mammal glucose homeostasis via liver and pancreas beta cells. In a juvenile diabetic case that case is referred to as MODY2, mutation of a glucokinase gene has been found, and the glucokinase activity reduction causes the blood-glucose level increase [for example, see Vionnet N. et al's "Nonsense mutation in the glucokinase gene causes early-onset non-indulin-dependent diabetes mellitus", Nature Genetics, Vol, 356, 1992, pp. 721-722]. On the other hand, a pedigree having mutation of increasing glucokinase activity has been found, and those of the family line show low blood-glucose level symptoms.

Form these, glucokinase acts as a glucose sensor and plays an important role in glucose homeostasis also in humans. On the other hand, blood-glucose level control by utilizing a glucokinase sensor system may be possible in many type-II diabetes patients. A glucokinase-activating substance may be expected to have an insulin secretion promoting effect in pancreas beta cells and have a sugar take-up accelerating and sugar release inhibiting activity in liver, And therefore it may be useful as a remedy for type-II diabetes patients.

Recently, it has become clarified that pancreas beta cell-type gulcokinase is limitedly expressed locally in rat brains, especially in ventromedial hypothalamus (VMH) thereof. About 20% neurocytes in VMH are referred to as glucose-resonsive neurons, and heretofore it has been considered they may play an important role in body weight control. When glucose is administered to a rat brain, then it reduces the amount of ingestion; but when glucose metabolism is retarded through intracerebral administration of glucosamine, a glucose analogue, then it cause hyperphagia.

From an electrophysiological experiment, it is admitted that glucose-responsive neurons are activated in accordance with a physiological glucose concentration change (5-20 mM), but when glucose metabolisns is inhibited by glucosamine or the like, and then their activity is retarded. In the glucose concentration-sensitive system in VMH, a glucose-mediated mechanism is anticipated like the insulin secretion in pancreas beta cells. Accordingly, there may be a possibility that a substance for glucokinase activation in VMH, in addition to liver and pancreas beta cells, may be effective not only for blood-glucose level correction but also for solution of obedity that is problematic in many type-II diabetes patients.

From the above description, a compound having a glucokinase activation effect is useful for remedies and/or preventives for diabetes, or for remedies and/or preventives for chronic complications of diabetes such as retinopathy, nephropathy, neurosis, ischemic cardiopathy, arterisclerosis, and further for remedies and/or preventives for obesity.

SUMMARY OF THE INVENTION

The present invention provides compounds for increasing glucokinase activities and their use in manufacturing a medicament.

The present invention provides a compound of the following Formula (I). The compound includes compounds of Formula (I), pharmaceutically acceptable salts thereof, solvates thereof, chelates thereof, non-covalent complexes thereof or, produgs of the compounds mentioned above, or the mixture of any form above mentioned,

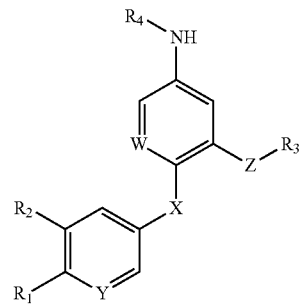

Formula (I)

wherein

W and Y are independently selected from N or C;

X is selected from O or S;

Z is selected from C, N, O or S;

R₁ is selected from the group consisting of —H, alkanyl, substituted alkanyl, alkenyl, substituted alkenyl, alkynyl, substituted alkynyl, alkoxy, substituted alkoxy, C(=O)R₅, SR₅, SO₂R₅, or haloalkyl; R₅ is selected from the group consisting of: lower alkanyl, substituted lower alkanyl, alkoxy, substituted alkoxy or NR₆R₇; R₆ and R₇ are independently selected from the group consisting of: —H, lower alkanyl, substituted lower alkanyl, or R₆ and R₇ can join together to from a 3 to 6 membered ring or a substituted 3 to 6 membered ring;

R₂ is selected from the group consisting of —H, alkanyl, substituted alkanyl, halogen or haloalkyl;

R₃ is selected from the group consisting of substituted alkanyl, alkenyl, substituted alkenyl, alkynyl, substituted alkynyl, cycloalkyl, substituted cycloalkyl, heterocycloalkyl or substituted heterocycloalkyl;

R₄ is selected from the group consisting of heteroaryl or substituted heteroaryl, wherein at least one ortho atom of the heteroaryl connected with NH fragment in Formula (I) is N.

In a preferred embodiment of the present invention, W is C.

In a particularly preferred embodiment of the present invention, W is C and Y is C. In a more preferred embodiment of the present invention, W is C, Y is C and X is O. In an even more preferred embodiment of the present invention, W is C, Y is C, X is O and Z is C.

In another particularly preferred embodiment of the present invention, W is C and Y is N. In a more preferred embodiment of the present invention, W is C, Y is N and X is O. In an even more preferred embodiment of the invention, W is C, Y is N, X is O and Z is C.

In a preferred embodiment of the present invention, W is N.

In a particularly preferred embodiment of the present invention, W is N and Y is C. In a more preferred embodiment of the present invention, W is N, Y is C and X is O. In an even more preferred embodiment of the present invention, W is N, Y is C, X is O and Z is C.

In another particularly preferred embodiment of the present invention, W is N and Y is N. In a more preferred embodiment of the present invention, W is N, Y is N and X is O. In an even more preferred embodiment of the present invention, W is N, Y is N, X is O and Z is C.

In a preferred embodiment of the present invention, X is O.

In a preferred embodiment of the present invention, Y is C.

In a preferred embodiment of the present invention, Y is N.

In a preferred embodiment of the present invention, Z is N.

In a more preferred embodiment of the present invention, R₁ is selected from —H, lower alkanyl, substituted lower alkanyl, lower alkenyl, substituted lower alkenyl, lower alkynyl, substituted lower alkynyl, C₁₋₆alkoxy or substituted C₁₋₆alkoxy. In a particularly preferred embodiment of the present invention, R₁ is selected from —H, lower alkanyl, substituted lower alkanyl, lower alkenyl, substituted lower alkenyl, lower alkynyl, substituted lower alkynyl, C₁₋₆ alkoxy or substituted C₁₋₆alkoxy; R₂ is —H; R₃ is selected from the group consisting of cycloalkyl, substituted cycloalkyl, heterocycloalkyl or substituted heterocycloalkyl; and R₄ is a 5- or 6-membered heteroaryl. In a more preferred embodiment of the present invention, R₁ is selected from:

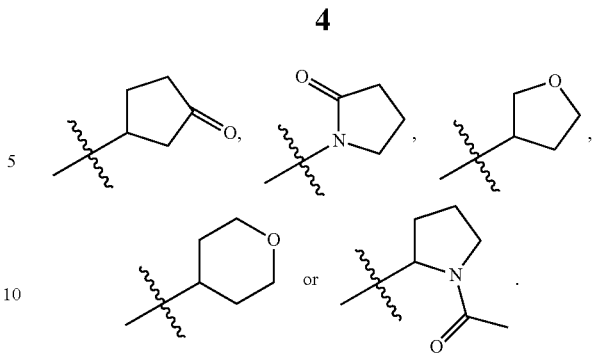

In a more preferred embodiment of the present invention, R₃ is selected from —H, C₁₋₃alkanyl, substituted C₁₋₃alkanyl, C₁₋₃alkoxyl or substituted C₁₋₃alkoxyl.

In yet another more preferred embodiment of the present invention, R₁ is —H.

In yet another more preferred embodiment of the present invention, R₁ is selected from C(=O)R₅, SR₅, SO₂R₅ or haloalkyl, wherein R₅ is selected from C₁₋₃alkanyl, substituted C₁₋₃alkanyl, C₁₋₆alkoxy, substituted C₁₋₆alkoxy or NR₆R₇. In a particularly preferred embodiment of the present invention, R₁ is selected from C(=O)R₅, SR₅, SO₂R₅ or haloalkyl; R₅ is selected from C₁₋₃alkanyl, substituted C₁₋₃alkanyl, C₁₋₆alkoxy, substituted C₁₋₆alkoxy or, wherein R₆ and R₇ are indepented selected from —H, lower alkanyl, substituted lower alkanyl, or R₆ and R₇ can join together to form a 3 to 6 membered ring or a substituted 3 to 6 membered ring; R₂ is —H; R₃ is selected from cycloalkanyl, substituted cycloalkanyl, heterocycloalkyl, substituted heterocycloalkyl; and R₄ is a 5- or 6-membered heteroaryl. In a more preferred embodiment of the present invention, R₃ is selected from:

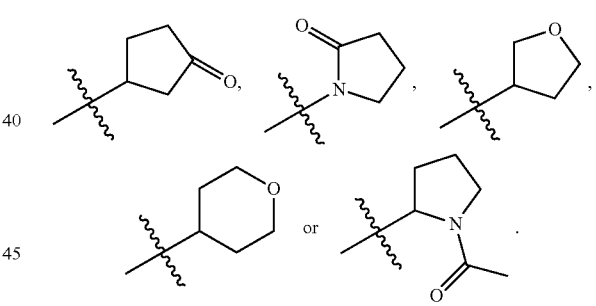

In an even more preferred embodiment of the present invention, R₁ is C(=O)R₅, and R₅ is NR₆R₇, wherein R₆ and R₇ are independently selected from —H, lower alkanyl, substituted lower alkanyl, or R₆ and R₇ can join together to form a 3 to 6 membered ring or a substituted 3 to 6 membered ring. In another even more preferred embodiment of the invention, R₁ is C(=O)R₅, and R₅ is C₁₋₃alkanyl.

In another more preferred embodiment of the present invention, R₁ is selected from C(=O)R₅, SR₅, SO₂R₅ or haloalkyl, wherein R₅ is selected from C₁₋₃alkanyl, substituted C₁₋₃alkanyl, C₁₋₆alkoxy, substituted C₁₋₆alkoxy or NR₆R₇, and R₆ and R₇ are independently selected from —H, C₁₋₄alkanyl or substituted C₁₋₄alkanyl.

In yet another even more preferred embodiment of the present invention, R₁ is selected from C(=O)R₅, SR₅, SO₂R₅ or haloalkyl, wherein R₅ is selected from C₁₋₃alkanyl, substituted C₁₋₃alkanyl, C₁₋₆alkoxy, substituted C₁₋₆alkoxy or NR₆R₇, and R₆ and R₇ can join together to form a 3 to 6 membered ring or a substituted 3 to 6 membered ring. Preferably, the 3 to 6 membered ring or substituted 3 to 6 membered ring is a hetero ring which contains heteroatoms selected from O or S.

In a more preferred embodiment of the present invention, $R_2$ is —H.

In a more preferred embodiment of the present invention, $R_2$ is selected from lower alkanyl or substituted lower alkanyl.

In a more preferred embodiment of the present invention, $R_2$ is haloalkyl, with more preferably halomethyl, haloethyl or halopropyl.

In a more preferred embodiment of the present invention, $R_3$ is selected from substituted lower alkanyl, lower alkenyl, substituted lower alkenyl, lower alkynyl or substituted lower alkynyl. With preferably, $R_3$ is selected from substituted $C_{1-3}$alkanyl, $C_{2-4}$alkenyl, or substituted $C_{2-4}$alkenyl.

In a more preferred embodiment of the invention, $R_3$ is selected from cycloalkanyl, substituted cycloalkanyl, heterocycloalkyl or substituted heterocycloalkyl.

In a more preferred embodiment of the present invention, $R_3$ is selected from:

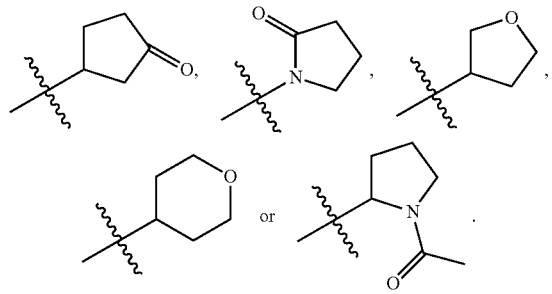

In another more preferred embodiment of the present invention, $R_4$ is a 5- or 6-membered heteroaryl.

Most preferably, the compound of the present invention is selected from:
1-(2-(6-(methylsulfonyl)pyridin-3-yloxy)-5-(pyridin-2-ylamino)benzyl)pyrrolidin-2-one;
N-ethyl-6-(4-(6-(methylsulfonyl)pyridin-3-yloxy)-3-((2-oxopyrrolidin-1-yl)methyl)phenylamino)nicotinamide;
1-(2-(6-(methylsulfonyl)pyridin-3-yloxy)-5-(5-phenylpyridin-2-ylamino)benzyl)pyrrolidin-2-one;
1-(2-(6-(methylsulfonyl)pyridin-3-yloxy)-5-(5-(trifluoromethyl)pyridin-2-ylamino)benzyl)pyrrolidin-2-one;
6-(4-(6-(methylsulfonyl)pyridin-3-yloxy)-3-((2-oxopyrrolidin-1-yl)methyl)phenylamino)nicotinonitrile;
6-(4-(6-(methylsulfonyl)pyridin-3-yloxy)-3-((2-oxopyrrolidin-1-yl)methyl)phenylamino)nicotinic acid;
ethyl 6-(4-(6-(methylsulfonyl)pyridin-3-yloxy)-3-((2-oxopyrrolidin-1-yl)methyl)phenylamino)nicotinate;
1-(5-(5-methylpyridin-2-ylamino)-2-(6-(methylsulfonyl)pyridin-3-yloxy)benzyl)pyrrolidin-2-one;
1-(2-(6-(methylsulfonyl)pyridin-3-yloxy)-5-(pyrazin-2-ylamino)benzyl)pyrrolidin-2-one;
1-(5-(3-methyl-1,2,4-thiadiazol-5-ylamino)-2-(6-(methylsulfonyl)pyridin-3-yloxy)benzyl)pyrrolidin-2-one;
1-(5-(1H-imidazol-4-ylamino)-2-(6-(methylsulfonyl)pyridin-3-yloxy)benzyl)pyrrolidin-2-one;
1-(5-(5-methoxypyridin-2-ylamino)-2-(6-(methylsulfonyl)pyridin-3-yloxy)benzyl)pyrrolidin-2-one;
1-(2-(6-(methylsulfonyl)pyridin-3-yloxy)-5-(5-methylthiazol-2-ylamino)benzyl)pyrrolidin-2-one;
1-(2-(6-(methoxymethyl)pyridin-3-yloxy)-5-(pyridin-2-ylamino)benzyl)pyrrolidin-2-one;
N-ethyl-6-(4-(6-(methoxymethyl)pyridin-3-yloxy)-3-((2-oxopyrrolidin-1-yl)methyl)phenylamino)nicotinamide;
1-(2-(6-(methoxymethyl)pyridin-3-yloxy)-5-(5-phenylpyridin-2-ylamino)benzyl)pyrrolidin-2-one;
1-(2-(6-(methoxymethyl)pyridin-3-yloxy)-5-(5-(trifluoromethyl)pyridin-2-ylamino)benzyl)pyrrolidin-2-one;
6-(4-(6-(methoxymethyl)pyridin-3-yloxy)-3-((2-oxopyrrolidin-1-yl)methyl)phenylamino)nicotinonitrile;
6-(4-(6-(methoxymethyl)pyridin-3-yloxy)-3-((2-oxopyrrolidin-1-yl)methyl)phenylamino)nicotinic acid;
ethyl 6-(4-(6-(methoxymethyl)pyridin-3-yloxy)-3-((2-oxopyrrolidin-1-yl)methyl)phenylamino)nicotinate;
1-(2-(6-(methoxymethyl)pyridin-3-yloxy)-5-(5-methylpyridin-2-ylamino)benzyl)pyrrolidin-2-one;
1-(2-(6-(methoxymethyl)pyridin-3-yloxy)-5-(pyrazin-2-ylamino)benzyl)pyrrolidin-2-one;
1-(2-(6-(methoxymethyl)pyridin-3-yloxy)-5-(3-methyl-1,2,4-thiadiazol-5-ylamino)benzyl)pyrrolidin-2-one;
1-(5-(1H-imidazol-4-ylamino)-2-(6-(methoxymethyl)pyridin-3-yloxy)benzyl)pyrrolidin-2-one;
1-(2-(6-(methoxymethyl)pyridin-3-yloxy)-5-(5-methylthiazol-2-ylamino)benzyl)pyrrolidin-2-one;
1-(2-(6-(morpholinosulfonyl)pyridin-3-yloxy)-5-(5-(trifluoromethyl)pyridin-2-ylamino)benzyl)pyrrolidin-2-one;
N-ethyl-5-(2-((2-oxopyrrolidin-1-yl)methyl)-4-(5-(trifluoromethoxy)pyridin-2-ylamino)phenoxy)picolinamide;
1-(2-(5-chloro-6-methylpyridin-3-yloxy)-5-(5-chloropyridin-2-ylamino)benzyl)pyrrolidin-2-one;
ethyl 6-(4-(4-(methylsulfonyl)phenoxy)-3-((3-oxocyclopentyl)methyl)phenylamino)nicotinate;
3-(2-(4-(methylsulfonyl)phenoxy)-5-(5-methylthiazol-2-ylamino)benzyl)cyclopentanone;
3-(2-(4-(methylsulfonyl)phenoxy)-5-(pyrazin-2-ylamino)benzyl)cyclopentanone;
3-(5-(3-methyl-1,2,4-thiadiazol-5-ylamino)-2-(4-(methylsulfonyl)phenoxy)benzyl)cyclopentan one;
3-(5-(1H-imidazol-4-ylamino)-2-(4-(methylsulfonyl)phenoxy)benzyl)cyclopentanone;
3-(2-(4-(methylsulfonyl)phenoxy)-5-(5-(trifluoromethyl)pyridin-2-ylamino)benzyl)cyclopentanone;
N-(6-(4-(methylsulfonyl)phenoxy)-5-((tetrahydrofuran-3-yl)methyl)pyridin-3-yl)pyridin-2-amine;
N-ethyl-6-(6-(4-(methylsulfonyl)phenoxy)-5-((tetrahydrofuran-3-yl)methyl)pyridin-3-ylamino) nicotinamide;
N-(6-(4-(methylsulfonyl)phenoxy)-5-((tetrahydrofuran-3-yl)methyl)pyridin-3-yl)-5-phenylpyridin-2-amine;
N-(6-(4-(methylsulfonyl)phenoxy)-5-((tetrahydrofuran-3-yl)methyl)pyridin-3-yl)-5-(trifluoromethyl)pyridin-2-amine;
6-(6-(4-(methylsulfonyl)phenoxy)-5-((tetrahydrofuran-3-yl)methyl)pyridin-3-ylamino)nicotinonitrile;
6-(6-(4-(methylsulfonyl)phenoxy)-5-((tetrahydrofuran-3-yl)methyl)pyridin-3-ylamino)nicotinic acid;
ethyl 6-(4-(4-(methylsulfonyl)phenoxy)-3-((tetrahydro-2H-pyran-4-yl)methyl)phenylamino)nicotinate;
N-(4-(4-(methylsulfonyl)phenoxy)-3-((tetrahydro-2H-pyran-4-yl)methyl)phenyl)-5-(trifluoromethyl)pyridin-2-amine;
N-(4-(4-(methylsulfonyl)phenoxy)-3-((tetrahydro-2H-pyran-4-yl)methyl)phenyl)pyrazin-2-amine;
3-methyl-N-(4-(4-(methylsulfonyl)phenoxy)-3-((tetrahydro-2H-pyran-4-yl)methyl)phenyl)-1,2,4-thiadiazol-5-amine;
N-(4-(4-(methylsulfonyl)phenoxy)-3-((tetrahydro-2H-pyran-4-yl)methyl)phenyl)-1H-imidazol-4-amine;
5-methyl-N-(4-(4-(methylsulfonyl)phenoxy)-3-((tetrahydro-2H-pyran-4-yl)methyl)phenyl)thiazol-2-amine;

ethyl 6-(3-((1-acetylpyrrolidin-2-yl)methyl)-4-(4-(methylsulfonyl)phenoxy)phenylamino)nicotinate;
1-(2-(2-(4-(methylsulfonyl)phenoxy)-5-(5-(trifluoromethyl)pyridin-2-ylamino)benzyl)pyrrolidin-1-yl)ethanone;
1-(2-(2-(4-(methylsulfonyl)phenoxy)-5-(pyrazin-2-ylamino)benzyl)pyrrolidin-1-yl)ethanone;
1-(2-(5-(3-methyl-1,2,4-thiadiazol-5-ylamino)-2-(4-(methylsulfonyl)phenoxy)benzyl)pyrrolidin-1-yl)ethanone;
1-(2-(5-(1H-imidazol-4-ylamino)-2-(4-(methylsulfonyl)phenoxy)benzyl)pyrrolidin-1-yl)ethanone;
1-(2-(2-(4-(methylsulfonyl)phenoxy)-5-(5-methylthiazol-2-ylamino)benzyl)pyrrolidin-1-yl)ethanone;
4-(4-(methylsulfonyl)phenoxy)-N1-(pyridin-2-yl)-N3-(tetrahydro-2H-pyran-4-yl)benzene-1,3-diamine;
4-(4-(methylsulfonyl)phenoxy)-N3-(tetrahydro-2H-pyran-4-yl)-N1-(5-(trifluoromethyl)pyridin-2-yl)benzene-1,3-diamine;
4-(4-(methylsulfonyl)phenoxy)-N1-(pyrimidin-4-yl)-N3-(tetrahydro-2H-pyran-4-yl)benzene-1,3-diamine;
3-methyl-N-(4-(4-(methylsulfonyl)phenylthio)-3-(tetrahydro-2H-pyran-4-yloxy)phenyl)-1,2,4-thiadiazol-5-amine;
N-(4-(4-(methylsulfonyl)phenylthio)-3-(tetrahydro-2H-pyran-4-yloxy)phenyl)-1H-imidazol-4-amine;
5-methyl-N-(4-(4-(methylsulfonyl)phenylthio)-3-(tetrahydro-2H-pyran-4-yloxy)phenyl)thiazol-2-amine;
ethyl 6-(4-(4-(dimethylcarbamoyl)phenoxy)-3-((3-oxocyclopentyl)methyl)phenylamino)nicotinate;
N,N-dimethyl-4-(4-(5-methylthiazol-2-ylamino)-2-((3-oxocyclopentyl)methyl)phenoxy)benzamide;
N,N-dimethyl-4-(2-((3-oxocyclopentyl)methyl)-4-(pyrazin-2-ylamino)phenoxy)benzamide;
N,N-dimethyl-4-(4-(3-methyl-1,2,4-thiadiazol-5-ylamino)-2-(3-oxocyclopentyl)methyl)phenoxy)benzamide;
4-(4-(1H-imidazol-4-ylamino)-2-(3-oxocyclopentyl)methyl)phenoxy)-N,N-dimethylbenzamide;
N,N-dimethyl-4-(2-((3-oxocyclopentyl)methyl)-4-(5-(trifluoromethyl)pyridin-2-ylamino)phenoxy)benzamide;
N,N-dimethyl-5-(2-((2-oxopyrrolidin-1-yl)methyl)-4-(pyridin-2-ylamino)phenoxy)picolinamide;
5-(4-(5-(ethylcarbamoyl)pyridin-2-ylamino)-2-((2-oxopyrrolidin-1-yl)methyl)phenoxy)-N,N-dimethylpicolinamide;
N,N-dimethyl-5-(2-((2-oxopyrrolidin-1-yl)methyl)-4-(5-phenylpyridin-2-ylamino)phenoxy)picolinamide;
N,N-dimethyl-5-(2-((2-oxopyrrolidin-1-yl)methyl)-4-(5-(trifluoromethyl)pyridin-2-ylamino)phenoxy)picolinamide;
5-(4-(5-cyanopyridin-2-ylamino)-2-((2-oxopyrrolidin-1-yl)methyl)phenoxy)-N,N-dimethylpicolinamide;
6-(4-(6-(dimethylcarbamoyl)pyridin-3-yloxy)-3-((2-oxopyrrolidin-1-yl)methyl)phenylamino)nicotinic acid;
ethyl 6-(4-(6-(dimethylcarbamoyl)pyridin-3-yloxy)-3-((2-oxopyrrolidin-1-yl)methyl)phenylamino)nicotinate;
N,N-dimethyl-5-(4-(5-methylpyridin-2-ylamino)-2-((2-oxopyrrolidin-1-yl)methyl)phenoxy)picolinamide;
N,N-dimethyl-5-(2-((2-oxopyrrolidin-1-yl)methyl)-4-(pyrazin-2-ylamino)phenoxy)picolinamide;
N,N-dimethyl-5-(4-(3-methyl-1,2,4-thiadiazol-5-ylamino)-2-((2-oxopyrrolidin-1-yl)methyl)phenoxy)picolinamide;
5-(4-(1H-imidazol-4-ylamino)-2-(2-oxopyrrolidin-1-yl)methyl)phenoxy)-N,N-dimethylpicolinamide;
N,N-dimethyl-5-(4-(5-methylthiazol-2-ylamino)-2-((2-oxopyrrolidin-1-yl)methyl)phenoxy)picolinamide;
2-(6-(4-(6-(dimethylcarbamoyl)pyridin-3-yloxy)-3-((2-oxopyrrolidin-1-yl)methyl)phenylamino)pyridin-3-yl)acetic acid;
3-(6-(4-(6-(dimethylcarbamoyl)pyridin-3-yloxy)-3-((2-oxopyrrolidin-1-yl)methyl)phenylamino)pyridin-3-yl)propanoic acid;
5-(4-(5-methoxypyridin-2-ylamino)-2-((2-oxopyrrolidin-1-yl)methyl)phenoxy)-N,N-dimethylpicolinamide;
N,N-dimethyl-4-(5-(pyridin-2-ylamino)-3-((tetrahydrofuran-3-yl)methyl)pyridin-2-yloxy)benzamide;
6-(6-(4-(dimethylcarbamoyl)phenoxy)-5-((tetrahydrofuran-3-yl)methyl)pyridin-3-ylamino)-N-ethylnicotinamide;
N,N-dimethyl-4-(5-(5-phenylpyridin-2-ylamino)-3-((tetrahydrofuran-3-yl)methyl)pyridin-2-yl oxy)benzamide;
N,N-dimethyl-4-(3-((tetrahydrofuran-3-yl)methyl)-5-(5-(trifluoromethyl)pyridin-2-ylamino)pyridin-2-yloxy)benzamide;
4-(5-(5-cyanopyridin-2-ylamino)-3-((tetrahydrofuran-3-yl)methyl)pyridin-2-yloxy)-N,N-dimethylbenzamide;
6-(6-(4-(dimethylcarbamoyl)phenoxy)-5-((tetrahydrofuran-3-yl)methyl)pyridin-3-ylamino)nicotinic acid;
6-(4-(4-(dimethylcarbamoyl)phenoxy)-3-((tetrahydro-2H-pyran-4-yl)methyl)phenylamino)nicotinic acid;
N,N-dimethyl-4-(2-((tetrahydro-2H-pyran-4-yl)methyl)-4-(5-(trifluoromethyl)pyridin-2-ylamino)phenoxy)benzamide;
N,N-dimethyl-4-(4-(pyrazin-2-ylamino)-2-((tetrahydro-2H-pyran-4-yl)methyl)phenoxy)benzamide;
N,N-dimethyl-4-(4-(3-methyl-1,2,4-thiadiazol-5-ylamino)-2-((tetrahydro-2H-pyran-4-yl)methyl)phenoxy)benzamide;
4-(4-(1H-imidazol-4-ylamino)-2-((tetrahydro-2H-pyran-4-yl)methyl)phenoxy)-N,N-dimethylbenzamide;
N,N-dimethyl-4-(4-(5-methylthiazol-2-ylamino)-2-((tetrahydro-2H-pyran-4-yl)methyl)phenoxy)benzamide;
6-(3-((1-acetylpyrrolidin-2-yl)methyl)-4-(4-(dimethylcarbamoyl)phenoxy)phenylamino)nicotinic acid;
4-(2-((1-acetylpyrrolidin-2-yl)methyl)-4-(5-(trifluoromethyl)pyridin-2-ylamino)phenoxy)-N,N-dimethylbenzamide;
4-(2-((1-acetylpyrrolidin-2-yl)methyl)-4-(pyrazin-2-ylamino)phenoxy)-N,N-dimethylbenzamide;
2-(6-(6-(4-(dimethylcarbamoyl)phenoxy)-5-((tetrahydrofuran-3-yl)methyl)pyridin-3-ylamino)pyridin-3-yl)acetic acid;
3-(6-(6-(4-(dimethylcarbamoyl)phenoxy)-5-((tetrahydrofuran-3-yl)methyl)pyridin-3-ylamino)pyridin-3-yl)propanoic acid;
2-(6-(4-(4-(dimethylcarbamoyl)phenoxy)-3-((tetrahydro-2H-pyran-4-yl)methyl)phenylamino)pyridin-3-yl)acetic acid;
3-(6-(4-(4-(dimethylcarbamoyl)phenoxy)-3-((tetrahydro-2H-pyran-4-yl)methyl)phenylamino)pyridin-3-yl)propanoic acid;
2-(6-(3-((1-acetylpyrrolidin-2-yl)methyl)-4-(4-(dimethylcarbamoyl)phenoxy)phenylamino)pyridin-3-yl)acetic acid;
3-(6-(3-((1-acetylpyrrolidin-2-yl)methyl)-4-(4-(dimethylcarbamoyl)phenoxy)phenylamino)pyridin-3-yl)propanoic acid;
2-(6-(4-(6-(methylsulfonyl)pyridin-3-yloxy)-3-((2-oxopyrrolidin-1-yl)methyl)phenylamino)pyridin-3-yl)acetic acid;
3-(6-(4-(6-(methylsulfonyl)pyridin-3-yloxy)-3-((2-oxopyrrolidin-1-yl)methyl)phenylamino)pyridin-3-yl)propanoic acid;
2-(6-(4-(6-(methoxymethyl)pyridin-3-yloxy)-3-((2-oxopyrrolidin-1-yl)methyl)phenylamino)pyridin-3-yl)acetic acid; or 3-(6-(4-(6-(methoxymethyl)pyridin-3-yloxy)-3-((2-oxopyrrolidin-1-yl)methyl)phenylamino)pyridin-3-yl)propanoic acid.

We found any one of compound of the present invention has a glucokinase activation $EC_{50}$ value of 50 μM or less in the presence of 5 mM glucose. With particularly, the compounds of the present invention has a glucokinase activation $EC_{50}$ value of 5 μM or less in the presence of 5 mM glucose.

The present invention also provides a method of modulating glucokinase levels or activities in animals or humans by administering to the subject at least one compound of Formula (I).

The present invention further provides a method for treating and/or preventing type II diabetes or related disease thereof, by administering to the subject a therapeutically effective amount of the compound of Formula (I). The present invention further provides a method for treating and/or preventing type I diabetes or related disease thereof, by administering to the subject a therapeutically effective amount of the compound of Formula (I).

The present invention further provides a method for treating and/or preventing obesity or related disease thereof, by administering to the subject a therapeutically effective amount of the compound of Formula (I).

The present invention also provides the use of the compound of Formula (I) of the present invention in manufacturing a medicament. Particularly, the present invention provides the use of the compounds of Formula (I) in manufacturing a medicament for modulating glucokinase levels or activities in animals or humans.

The present invention further provides the use of the compound of Formula (I) in manufacturing a medicament for the treatment and/or prevention of type II diabetes or related disease thereof.

The present invention further provides the use of the compound in manufacturing a medicament for the treatment and/or prevention of type I diabetes or related disease thereof.

The present invention further provides the use of the compound in manufacturing a medicament for the treatment and/or prevention of obesity or related disease thereof. The present invention also further provides a pharmaceutical composition comprising a therapeutically effective amount of one or more of compounds of Formula (I), and at least one pharmaceutically acceptable excipient, adjuvant or carrier.

The present invention further provides the use of the pharmaceutical composition in manufacturing a medicament. Particularly, the present invention further provides the use of the pharmaceutical composition in manufacturing a medicament for modulating glucokinase levels or activities in animals or humans.

The present invention further provides the use of the pharmaceutical composition in manufacturing a medicament for the treatment or prevention of type II diabetes and/or related disease thereof.

The present invention further provides the use of the pharmaceutical composition in manufacturing a medicament for the treatment or prevention of type I diabetes and/or related disease thereof.

The present invention further provides the use of the pharmaceutical composition in manufacturing a medicament for the treatment and/or prevention of obesity or related disease thereof.

In addition, the present invention also further provides a method of modulating glucokinase levels or activities in animals or humans by administering to the subject a therapeutically effective amount of the pharmaceutical composition of the present invention.

The present invention also provides a method for the treatment and/or prevention of type II diabetes or related disease thereof, by administering to the subject a therapeutically effective amount of the pharmaceutical composition of the present invention.

The invention also provides a method for the treatment and/or prevention of type I diabetes or related disease thereof, by administering to the subject a therapeutically effective amount of the pharmaceutical composition of the present invention.

The present invention also provides a method for the treatment and/or prevention of obesity or related disease thereof, by administering to the subject a therapeutically effective amount of the pharmaceutical composition of the present invention.

BRIEF DESCRIPTION OF THE DRAWINGS

FIG. 1 shows the glucose levels in some examples.

DETAILED DESCRIPTION OF THE INVENTION

As used herein, the following underlined terms are intended to have the following meanings:

"$C_{m-n}$" (where m and n are integers) refers to a radical inclusively containing from m number of carbon atoms to n number of carbon atoms. For example, $C_{1-3}$ denotes a radical containing 1, 2 or 3 carbon atoms.

"n membered" or "n-membered" (where n are integers) refers to the atom numbers in a ring. For example, pyridyl is a 6-membered aryl.

The term "alkyl" refers to a saturated or unsaturated, branched or straight-chain monovalent hydrocarbon group derived by the removal of one hydrogen atom from a single carbon atom of a parent alkane, alkene or alkyne. Where a specific level of saturation is intended, the nomenclature "alkanyl", "alkenyl" or "alkynyl" is used. Typical alkyl groups include, but are not limited to, methyl, ethyl, ethenyl, ethynyl, propyls such as propan-1-yl, and propan-2-yl, butyls such as butan-1-yl, butan-2-yl, 2-methyl-propan-1-yl, 2-methyl-propan-2-yl, tert-butyl, and the like. In certain embodiments, an alkyl group comprises from 1 to 20 carbon atoms. As used herein the term "lower alkyl" refers to an alkyl group comprising from 1 to 6 carbon atoms. Typical lower alkyl groups include, but are not limited to, methyl, ethyl, propyl, isopropyl, n-butyl, isobutyl, tert-butyl, s-butyl, pentyl, neopentyl or hexyl.

"Alkoxy" refers to —OR in which R is an alkyl. Typical alkoxy groups include, but are not limited to, methoxy, ethoxy, propoxy, butyloxy, cyclohexyloxy and the like. As used herein the term "lower alkoxy" refers to an alkoxy group comprising from 1 to 6 carbon atoms.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. For example, aryl includes 5- and 6-membered carbocyclic aromatic rings fused to a 5- to 7-membered heterocycloalkyl ring containing 1 or more heteroatoms selected from N, O, and S. In certain embodiments, an aryl group can comprise from 6 to 10 carbon atoms.

"Heteroaryl" refers to a monovalent heteroaromatic group derived by the removal of one hydrogen atom from a single atom of a parent heteroaromatic ring system. Heteroaryl encompasses: 5- to 7-membered aromatic, monocyclic rings containing one or more, for example, from 1 to 4, or in certain embodiments, from 1 to 3, heteroatoms selected from N, O, and S, with the remaining ring atoms being carbon; and polycyclic heterocycloalkyl rings containing one or more, for example, from 1 to 4, or in certain embodiments, from 1 to 3, heteroatoms selected from N, O, and S, with the remaining ring atoms being carbon and wherein at least one heteroatom is present in an aromatic ring. Particularly preferred heteroaryl groups are C3-C10 heteroaryl, include but are not limited to, pyrrolyl, furanyl, thienyl, pyridinyl, pyranyl, pyrazolyl, pyrimidinyl, imidazolyl, thiazolyl, pyrazolyl, oxazolyl, indolyl, benzofuranyl, benzothienyl, carbazolyl, quinolinyl, isoquinolinyl, purinyl and the like.

But, in any case, the heteroaryl and the aryl do not cross or include each other. Thereby, according to as defined above, if one or more full carbon aromatic ring fused with a heteroaryl is a heteroaryl, but not an aryl.

"Cycloalkyl" refers to a saturated or unsaturated, but non-aromatic, cyclic alkyl group. Where a specific level of saturation is intended, the nomenclature "cycloalkanyl", "cycloalkenyl" or "cycloalkynyl" is used. Typical cycloalkyl groups include, but are not limited to, groups derived from cyclopropane, cyclobutane, cyclopentane, cyclohexane, cyclohexene, and the like. In certain embodiments, the cycloalkyl group can be C3-10 cycloalkyl, such as, for example, C3-6 cycloalkyl.

"Heterocycloalkyl" refers to a saturated or unsaturated, but non-aromatic, cyclic alkyl group in which one or more carbon atoms (and any associated hydrogen atoms) are independently replaced with the same or different heteroatom and its associated hydrogen atoms, where appropriate. Typical heteroatoms to replace the carbon atom(s) include, but are not limited to, N, P, O, S, and Si. Where a specific level of saturation is intended, the nomenclature "heterocycloalkanyl" or "heterocycloalkenyl" is used. Typical heterocycloalkyl groups include, but are not limited to, groups derived from epoxides, imidazolidine, morpholine, piperazine, piperidine, pyrazolidine, pyrrolidine, quinuclidine, tetrahydrofuran, tetrahydropyran and the like. Substituted heterocycloalkyl also includes ring systems substituted with one or more oxo (=O) or oxide (—O—) substituents, such as piperidinyl N-oxide, morpholinyl-N-oxide, 1-oxo-1-thiomorpholinyl and 1,1-dioxo-1-thiomorpholinyl.

But, in any case, the heterocycloalkyl and the cycloalkyl do not cross or include each other. Thereby, according to as defined above, if one or more full carbon hydrocarbon ring fused with a hererocycloalkyl to form a bi- or multi- or spiro-cyclic ring, is still defined as a hererocycloalkyl.

"Halogen" refers to fluorine (F), chlorine (Cl), bromine (Br) or iodine (I) atoms.

"Halo" refers to a fluoro, chloro, bromo, or iodo group.

"Substituted" refers to a group in which one or more hydrogen atoms are each independently replaced with the same or different substituent(s). Typical substituents include, but are not limited to, X, $C_{3-20}$ cycloalkyl, —$OR_{13}$, $SR_{13}$, =O, =S, —$C(O)R_{13}$, —$C(S)R_{13}$, —$C(O)OR_{13}$, —$C(S)OR_{13}$, —$NR_{13}R_{14}$, —$C(O)NR_{13}R_{14}$, cyano, nitro, —$S(O)_2R_{13}$, —$OS(O_2)OR_{13}$, —$OS(O)_2R_{13}$, —$OP(O)(OR_{13})(OR_{14})$; wherein each X is independently a halogen (F, Cl, Br or I), and $R_{13}$ and $R_{14}$ is independently selected from —H, lower alkyl, lower haloalkyl. In some embodiments, the substituent(s) is independently selected from the group consisting of —F, —Cl, —Br, —I, —OH, trifluoromethoxy, ethoxy, propyloxy, iso-propyloxy, n-butyloxy, isobutyloxy, t-butyloxy, —$SCH_3$, —$SC_2H_5$, formaldehyde group, —C(OCH3), cyano, nitro, $CF_3$, —$OCF_3$, amino, dimethylamino, methyl thio, sulfonyl and acetyl. Particularly preferred substituent(s) is —F, —Cl or —Br.

As used herein, the "compound" of the present invention includes the compounds of Formula (I), and all pharmaceutically acceptable forms thereof. These pharmaceutically acceptable forms of the compounds include salts, solvates, non-covalent complexes, chelates, or produgs thereof, or the mixture of any form mentioned above.

As used herein, "pharmaceutically acceptable" refers to generally recognized for use in animals, and more particularly in humans.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

The present invention provides compounds regulating the glucokinase level or activity in animal(s) or a human, and using these compounds to manufacture medicaments for the treatment and/or prevention of diseases associated with glucokinase level or activity. These compounds are characteristic of relatively simple structures, convenient preparation and outstanding therapeutic effect. As a potential drug with low cost and convenient administration, it can be more widely applied, be more of help to patients for treating diseases and improving life quality.

EXAMPLES

The present invention is further exemplified, but not limited, by the following examples that illustrate the preparation of compounds of Formula (I) of the present invention.

The following examples are only used to disclose the preferred embodiments of the present invention, to help technicians in the art understand well, but are not used to limit the spirit and scope of the present invention. In the examples of the present invention, the approach or methods or the like is conventional in the art without specification. The compounds of the present invention can be prepared through, but not limited to, one or more of the following general reaction scheme:

General scheme I:

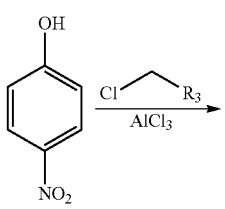

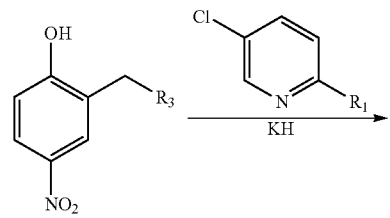
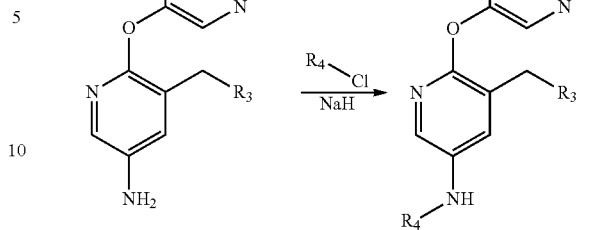
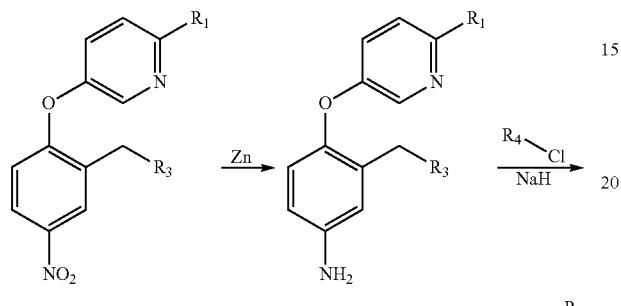
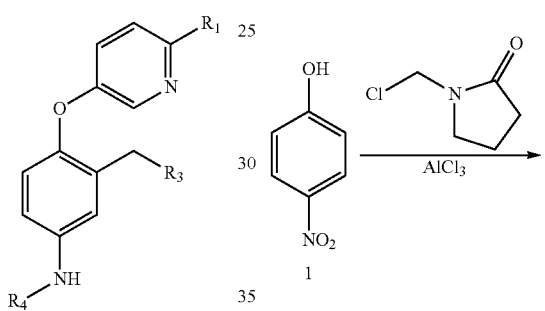
Example 1
Synthesis of 1-(2-(6-(methylsulfonyl)pyridin-3-yloxy)-5-(pyridin-2-ylamino)benzyl)pyrrolidin-2-one
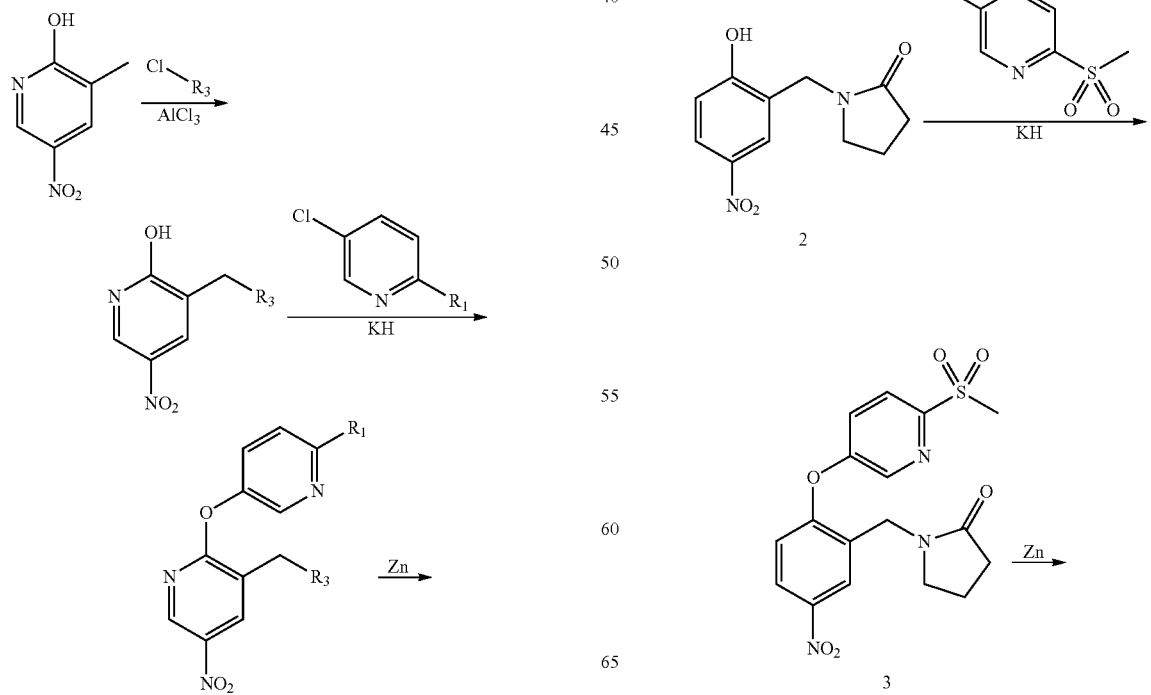

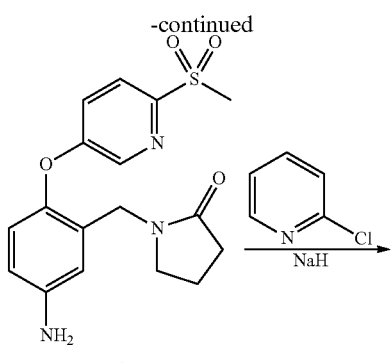

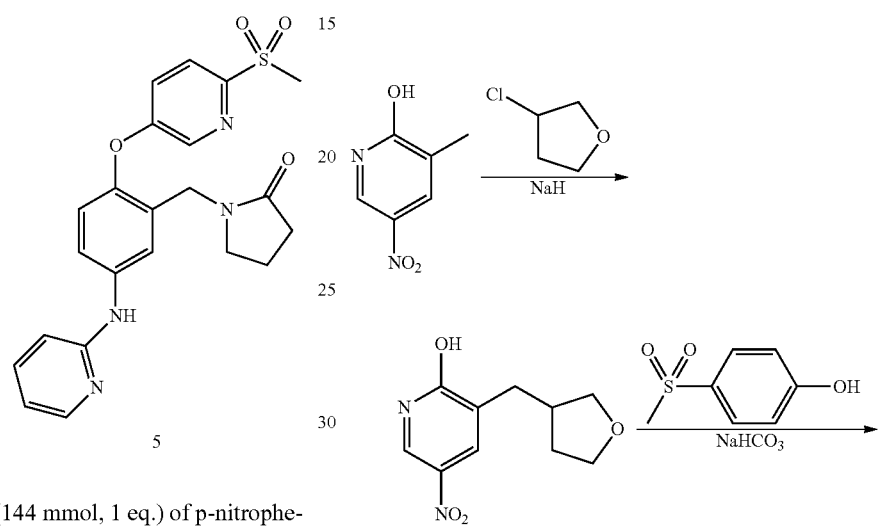

Under nitrogen gas, 20 g (144 mmol, 1 eq.) of p-nitrophenol was added into a 500 mL reaction flask, and dissolved in 200 mL of carbon disulfide, and then 20 g (144 mmol, 1 eq.) of anhydrous AlCl$_3$ was added. The mixture was refluxed and 19.2 g (144 mmol, 1 eq.) of N-chloromethyl cyclobutyramide was slowly added in drops. After about 2 hr. till reaction was complete, the reaction mixture was poured into crushed ice, stirred and filtered. The filtrate was run through column chromatography to obtain 12.1 g of white solid 2, with a yield of 45%.

236 mg (1.0 mmol, 1 eq.) of 2 and 20 mL of DMF were added into a reaction flask, and then 71 mg of 70% of KH (1.2 mmol, 1.2 eq.) was slowly added in, and stirred for 1 hr at rt. (room temperature). 273 mg (1.2 mmol, 1.2 eq.) 5-chloro-2-methylsulfonylpyridine was then added and stirred overnight till reaction completion verified by TLC, 10 mL of 50% ethanol was slowly added into the reaction mixture to quench the reaction. The solvent was removed by vacuum distillation, and the product was purified by column chromatography, to obtain 180 mg of 3, with a yield of 50%.

400 mg (1.02 mmol, 1 eq.) of 3, 40 mL of ethanol and 70 mg of raney nickel were added into a 100 mL hydrogen addition apparatus. The mixture was stirred, and subjected to nitrogen gas replacement twice, followed by hydrogen gas replacement once with the hydrogen pressure maintained at 4 atm. The reaction mixture was maintained at 50° C. until the hydrogen gas was no longer absorbed in the system. After removing catalyst by filtration and solvent by vacuum distillation, the product was purified by a flash chromatography to obtain 221 mg of 4, with a yield of 60%.

361 mg (1.0 mmol, 1 eq.) of 4 and 20 mL of DMF were added into a reaction flask, and then 43 mg of 70% NaH (1.2 mmol, 1.2 eq.) was slowly added and stirred for 1 hr. at rt. The reaction mixture was then added 136 mg (1.2 mmol, 1.2 eq.) of 2-chloropyridine, and stirred overnight till reaction completion verified by TLC. 10 mL of water was slowly added to quench the reaction. The solvent was removed by vacuum distillation, and the product was purified by column chromatography, to obtain 180 mg of final product 5, with a yield of 40%, and a LC-MS [M+H]-m/z of 439.

Example 35

Synthesis of N-(6-(4-(methylsulfonyl)phenoxy)-5-((tetrahydrofuran-3-yl)methyl)pyridin-3-yl)pyridin-2-amine

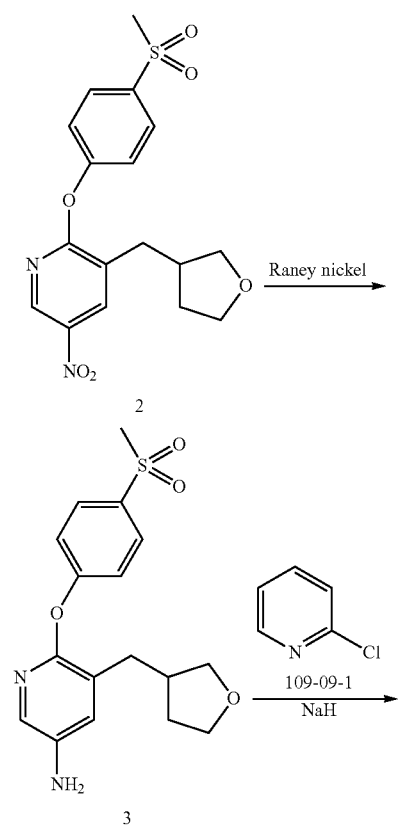

-continued

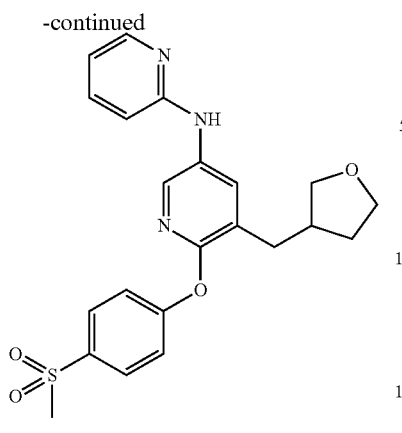

4

344 mg (2.0 mmol, 1 eq.) of 3-methyl-5-nitro-2-chloropyridine and 20 mL of DMF were added into a reaction flask, and then 86 mg of 70% NaH (2.4 mmol, 1.2 eq.) was slowly added. The mixture was stirred and heated to the temperature of 90° C. After 1 hr of reaction, 254 mg (2.4 mmol, 1.2 eq.) of 3-chloro-tetrahydrofuran was added and stirred overnight at 90° C., till reaction completion verified by TLC. 10 mL of 50% ethanol was then slowly added to quench the reaction. The solvent was removed by vacuum distillation, and the product was purified by a flash chromatography, to obtain 158 mg of 1, with a 33% yield.

Under nitrogen gas, 1.9 g (11 mmol, 1.1 eq) of o-methylsulfonyl phenol, 2.24 g (10 mmol, 1 eq.) of 1, 2.6 g (31.5 mmol, 3 eq.) of $NaHCO_3$ and 50 mL of ethanol were added into a reaction flask, and stirred and refluxed overnight, till reaction completion verified by TLC. The solvent was removed by vacuum distillation, and the residue was dissolved with dichloromethane, filtered to remove insoluble material(s), distilled in vacuum to remove solvent, and further purified by liquid chromatography, to obtain a 1.3 g of yellow solid 2, yielding 34%.

400 mg (1.06 mmol, 1 eq.) of 2, 40 mL of anhydrous ethanol and 70 mg of raney nickel were added into a 100 mL hydrogen addition apparatus. The mixture was stirred and subjected to nitrogen gas replacement twice, followed by hydrogen gas replacement once with the hydrogen pressure maintained at 4 atm. The reaction mixture was maintained at 50° C. until the hydrogen gas was no longer absorbed in the system. After removing catalyst by filtration and solvent by vacuum distillation, the product was purified by a flash chromatography to obtain 273 mg of 3, yielding 74%.

348 mg (1.0 mmol, 1 eq.) of 3 and 20 mL of DMF were added into a reaction flask, and then 43 mg of 70% NaH (1.2 mmol, 1.2 eq.) was slowly added, and stirred for 1 hr. at rt. The reaction mixture was then added 136 mg (1.2 mmol, 1.2 eq.) of 2-chloropyridine, and stirred overnight till reaction completion verified by TLC. 10 mL of water was slowly added to quench the reaction. The solvent was removed by vacuum distillation, and the product was purified by a flash chromatography to obtain 182 mg of 4, with a 43% yield. LC-MS [M+H]-m/z is 427.

Example 53

Synthesis of 4-(4-(methylsulfonyl)phenoxy)-N1-(pyridin-2-yl)-N3-(tetrahydro-2H-pyran-4-yl)benzene-1,3-diamine

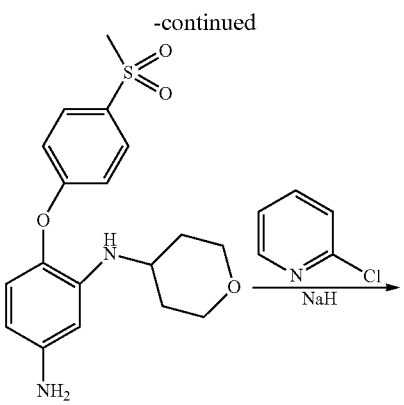

2H-tetrahydropyran was added and stirred overnight. After the reaction was complete, water was added and filtered to remove solvent. The product was purified by column chromatography to obtain 100 mg of 5, with a yield of 40%. and a LC-MS [M+H]-m/z of 441.

Example 56

Synthesis of 3-methyl-N-(4-(4-(methylsulfonyl)phenylthio)-3-(tetrahydro-2H-pyran-4-yloxy)phenyl)-1,2,4-thiadiazol-5-amine

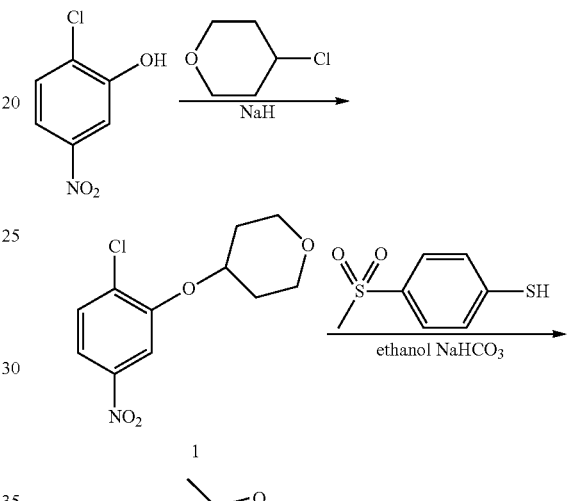

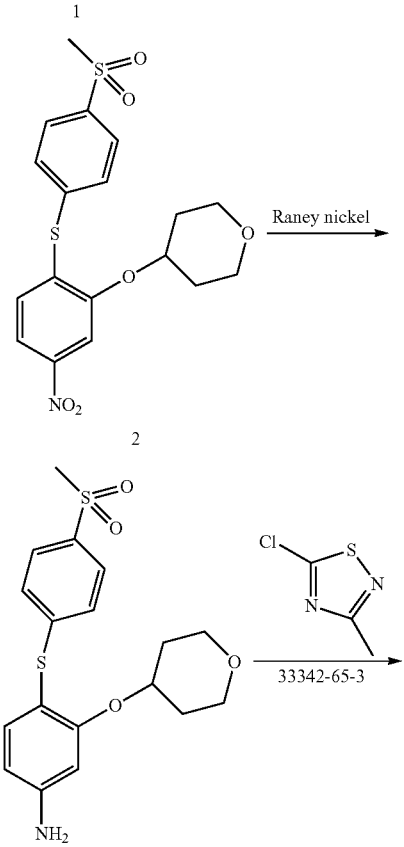

2 g (11.6 mmol, 1.1 eq.) of 4-(methyl-sulfonyl) phenol, 2.1 g (10.5 mmol, 1 eq.) of 1-chloro-2,4-dinitrobenzene, 2.6 g (31.5 mmol, 3 eq.) of NaHCO₃ and ethanol were added into a reaction flask, stirred and refluxed overnight. After the reaction was complete, the reaction mixture was filtered to remove the solvent, and washed by methylene chloride and purified by column chromatography to obtain 1.7 g of 1, with a yield of 50%.

253 mg (3.2 mmol, 1.1 eq.) of Na₂S was added into the solution of 1 g (2.9 mmol, 1 eq.) of 1 in ethanol, and stirred for 4 hr at rt. After the reaction was complete, the solvent was removed by vacuum distillation, and the product was purified by column chromatography to obtain 455 mg of 2, with a yield of 50%.

70 mg (1.76 mmol, 1.1 eq.) of NaH was added into the solution of 455 mg (1.4 mmol, 1 eq.) 2 in DMF, and stirred for 1 hr at rt. 211 mg (1.76 mmol, 1.1 eq.) of 4-chloro-2H-tetrahydropyran was then added and stirred overnight. After the reaction was complete, water was added, and then all the solvent was removed by filtration and the product was purified by column chromatography to obtain 942 mg of 3, with a yield of 60%.

151 mg (2.4 mmol, 2 eq.) of Zn and 133 mg (1.2 mmol, 1 eq.) of CaCl₂ were added into the solution of 500 mg (1.2 mmol, 1 eq.) of 3 in ethanol, and then stirred for 4 hr at rt. The solvent was removed by vacuum distillation, and the product was purified by column chromatography to obtain 230 mg of 4, yield 50%.

80 mg (1.98 mmol, 1.1 eq.) of NaH was added into the solution of 200 mg (1.8 mmol, 1 eq.) 4 in DMF, and stirred for 1 hr at rt. And then, 223 mg (1.98 mmol, 1.1 eq.) of 2-chloro- -continued

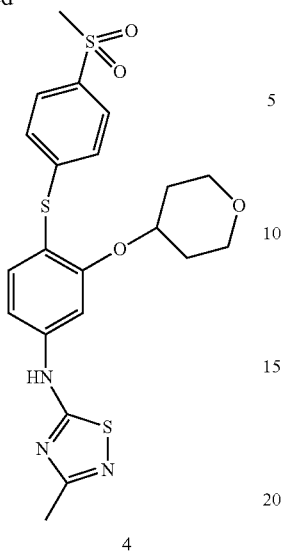

4

440 mg (12.7 mmol, 1.1 eq.) of NaH was added into the solution of 2 g (11.5 mmol, 1 eq.) 2-chloro-5-nitrophenol in DMF, and stirred for 1 hr at rt. And then, 1.5 g (12.7 mmol, 1.1 eq) of 4-chloro-2H-tetrahydropyran was added and stirred overnight. After the reaction was complete, water was added and filtered to remove solvent. The product was purified by column chromatography to obtain 1.7 g of 1, with a yield of 70%.

1 g (3.9 mmol, 1.1 eq.) of 4-(methylsulfonyl) phenol, 900 mg (10.5 mmol, 1 eq.) of 1-chloro 0.3-dinitrobenzene, 882 mg (10.5 mmol, 3 eq.) of NaHCO₃ and ethanol were added into a reaction flask, stirred and refluxed overnight. After the reaction was complete, the reaction mixture was filtered to remove the solvent, and the resulted solid was washed by methylene chloride twice and purified by column chromatography to obtain 477 mg of 2, with a yield of 30%.

93 mg (1.466 mmol, 2 eq.) of Zn and 81 mg (0.733 mmol, 1 eq.) of CaCl₂ were added into the solution of 300 mg (0.733 mmol, 1 eq.) of 2 in ethanol, and then stirred for 4 hr at rt. The solvent was removed by vacuum distillation, and the product was purified by column chromatography to obtain 110 mg of 3, with a yield of 40%.

12 mg (0.29 mmol, 1.1 eq.) of NaH was added into the solution of 100 mg (0.26 mmol, 1 eq.) 3 in DMF, and stirred for 1 hr at rt. And then, 267 mg (1.98 mmol, 1.1 eq.) of 3-chloro-2H-tetrahydropyran was added and stirred overnight. After the reaction was complete, water was added and filtered to remove solvent. The product was purified by column chromatography to obtain 75 mg of 4, with a yield of 60%, and LC-MS [M+H]-m/z of 479.

Example 65

Synthesis of N,N-dimethyl-5-(2-((2-oxopyrrolidin-1-yl)methyl)-4-(pyridin-2-ylamino)phenoxy)picolinamide

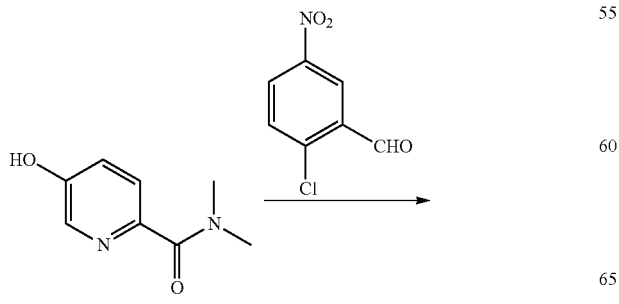

1

-continued

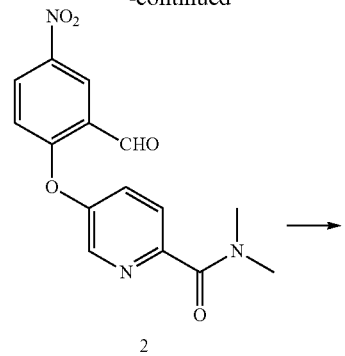

2

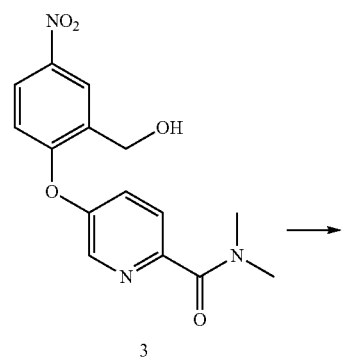

3

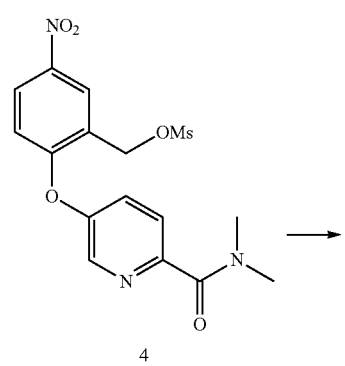

4

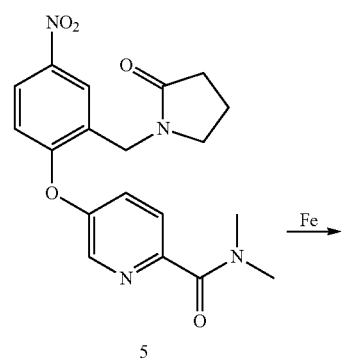

5

-continued

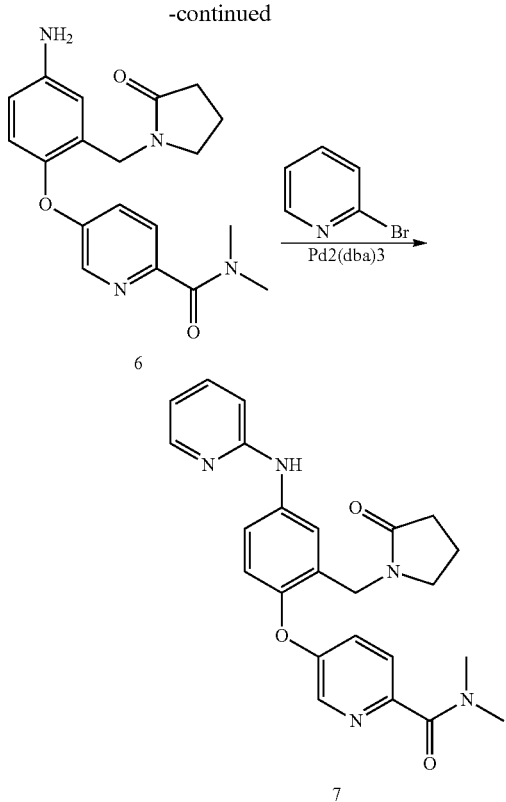

At 0° C., 0.59 g (70% oil dispersion) of NaH was added into 2.2 g of compound 1 in 40 mL of DMF, and stirred for 15 min. 2.45 g of 2-chloro-5-nitrobenzaldehyde was added into the mixture maintained at 0° C., and stirred for 30 min. The reaction mixture was poured into ice water, extracted with ethyl acetate, and the obtained organic layer was washed with saline water. After dried by anhydrous sodium sulfate and filtered, the solvent was removed, and the product was purified by column chromatography to obtain 3.80 g of 2, with a yield of 91%.

At rt., 0.50 g of NaBH$_4$ was added into the solution of 3.80 g 2 in 200 mL methanol, and stirred for 30 min.

After the solvent methanol was removed, water was added, then extracted with ethyl acetate, and the organic layer was washed with saline water. After dried by anhydrous sodium sulfate and filtered, the solvent was removed to obtain 2.64 g of 3, with a yield of 69%.

0.46 g of triethylamine was added into the solution of 0.44 g of 3 in 20 mL THF, followed by 0.23 mL of methyl sulfonyl chloride added in drops, and stirred for 30 min. The reaction mixture was extracted with ethyl acetate. The organic layer was washed with saline water, and dried by anhydrous sodium sulfate. After filtration, the solvent was removed to obtain 0.60 g of 4.

143 mg of (70% oil dispersion) of NaH was added into the solution of 620 mg pyrrolidone in 15 mL DMF, and stirred for 30 min at rt.

The mixture solution was cooled to below 0° C., and then 0.60 g of 4 was add, and stirred for 30 min at rt. The reaction solution was extracted with ethyl acetate, and the organic layer was washed with saline water. After dried by anhydrous sodium sulfate and filtered, the solvent was removed, and the product was purified by column chromatography to obtain 0.39 g of 5, with a two-step yield of 74%.

0.39 g of 5 was suspended in the solution of 0.88 g ammonium chloride in 40 mL water, and then heated to 90° C., 0.56 g of Fe powder was added and stirred for 30 min. The reaction mixture was cool down to rt., and K$_2$CO$_3$ was add, then extracted with ethyl acetate. After dried by anhydrous sodium sulfate and filtered, the solvent was removed, and the product was purified by column chromatography to obtain 0.28 g of 6, with a yield of 78%.

210 mg of 6,130 mg of 2-bromopyridine, 14 mg of Pd$_2$(dba)$_3$, 3.21 mg of BINAP, 147 mg of potassium tert-butanol and 2 mL of dioxane was mixed, and reacted overnight at 80° C. under nitrogen gas. The solvent was removed by distillation, and the product was purified by column chromatography to obtain 51 mg of final product 7, with a LC-MS[M+H]-m/z of 432, and a yield of 20%.

The following compounds listed in Table I can be prepared through similar procedures to those of the above examples:

TABLE I

| Example | Structure | Molecular Formula | Molecular Weight | Molecular Name | LC-MS [M + H](m/z) |
|---|---|---|---|---|---|
| 2 | 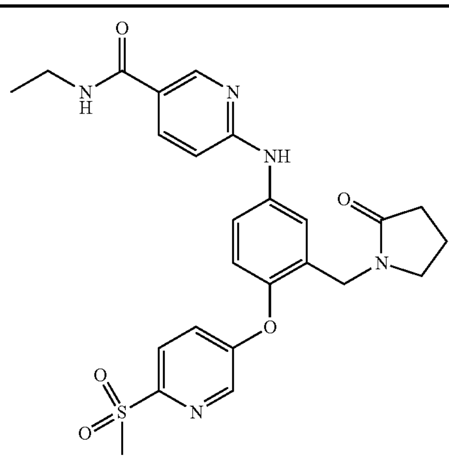 | C$_{25}$H$_{27}$N$_5$O$_5$S | 510 | N-ethyl-6-(4-(6-(methyl-sulfonyl)pyridin-3-yloxy)-3-((2-oxopyrrolidin-1-yl)methyl)phenylamino)nicotinamide | 511 |

TABLE I-continued

| Example | Structure | Molecular Formula | Molecular Weight | Molecular Name | LC-MS [M + H](m/z) |
|---|---|---|---|---|---|
| 3 | 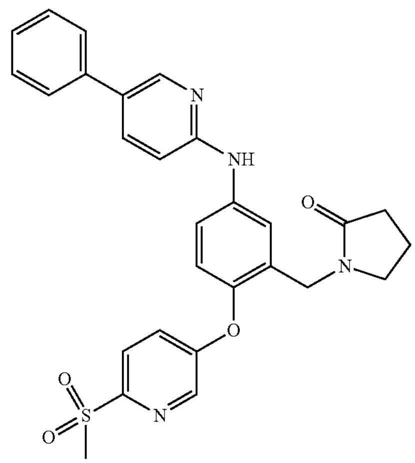 [SMILES: CS(=O)(=O)c1ccc(Oc2ccc(Nc3ccc(-c4ccccc4)cn3)cc2CN2CCCC2=O)cn1] | $C_{28}H_{26}N_4O_4S$ | 515 | 1-(2-(6-(methylsulfonyl)pyridin-3-yloxy)-5-(5-phenylpyridin-2-ylamino)benzyl)pyrrolidin-2-one | 516 |
| 4 | 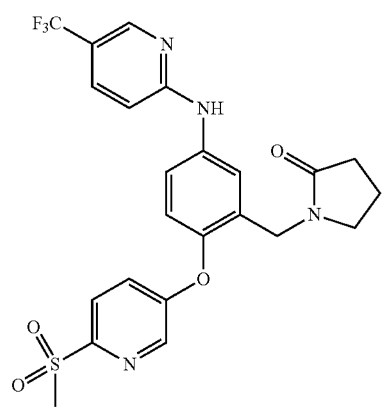 | $C_{23}H_{21}F_3N_4O_4S$ | 506 | 1-(2-(6-(methylsulfonyl)pyridin-3-yloxy)-5-(5-(trifluoromethyl)pyridin-2-ylamino)benzyl)pyrrolidin-2-one | 507 |
| 5 | 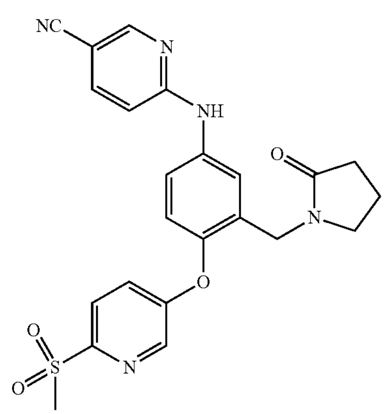 [SMILES: CS(=O)(=O)c1ccc(Oc2ccc(Nc3ccc(C#N)cn3)cc2CN2CCCC2=O)cn1] | $C_{23}H_{21}N_5O_4S$ | 464 | 6-(4-(6-(methylsulfonyl)pyridin-3-yloxy)-3-((2-oxopyrrolidin-1-yl)methyl)phenylamino)nicotinonitrile | 465 |

TABLE I-continued

| Example | Structure | Molecular Formula | Molecular Weight | Molecular Name | LC-MS [M + H](m/z) |
|---|---|---|---|---|---|
| 6 | 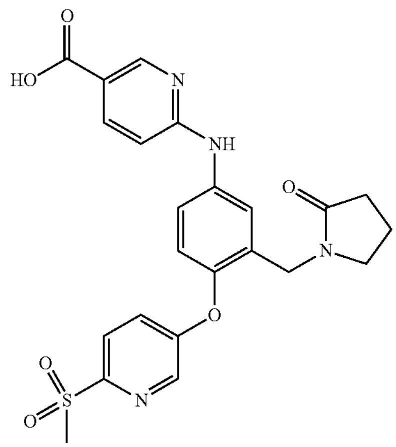 [SMILES: CS(=O)(=O)c1ccc(Oc2ccc(Nc3ccc(C(=O)O)cn3)cc2CN2CCCC2=O)cn1] | C₂₃H₂₂N₄O₆S | 483 | 6-(4-(6-(methylsulfonyl) pyridin-3-yloxy)-3-((2-oxopyrrolidin-1-yl)methyl) phenylamino) nicotinic acid | 484 |
| 7 | 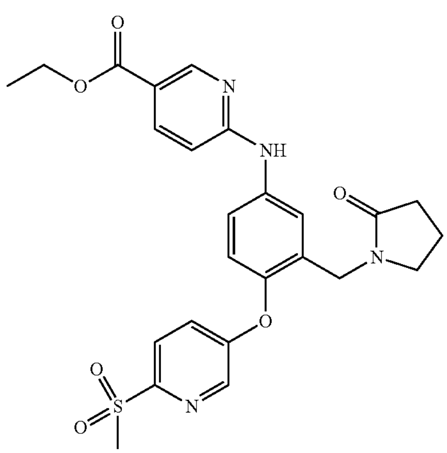 [SMILES: CCOC(=O)c1ccc(Nc2ccc(Oc3ccc(S(C)(=O)=O)nc3)c(CN3CCCC3=O)c2)nc1] | C₂₅H₂₆N₄O₆S | 511 | ethyl 6-(4-(6-(methylsulfonyl) pyridin-3-yloxy)-3-((2-oxopyrrolidin-1-yl)methyl) phenylamino) nicotinate | 512 |
| 8 | 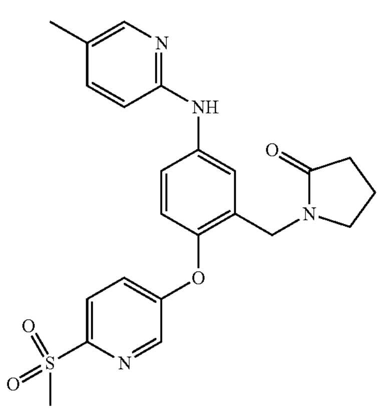 [SMILES: Cc1ccc(Nc2ccc(Oc3ccc(S(C)(=O)=O)nc3)c(CN3CCCC3=O)c2)nc1] | C₂₃H₂₄N₄O₄S | 453 | 1-(5-(5-methylpyridin-2-ylamino)-2-(6-(methylsulfonyl) pyridin-3-yloxy) benzyl)pyrrolidin-2-one | 454 |

TABLE I-continued

| Example | Structure | Molecular Formula | Molecular Weight | Molecular Name | LC-MS [M + H](m/z) |
|---------|-----------|-------------------|------------------|----------------|---------------------|
| 9 | 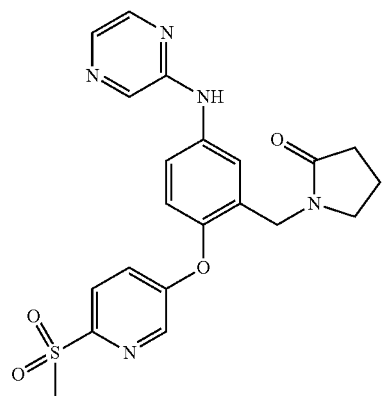 [SMILES: CS(=O)(=O)c1ccc(Oc2ccc(Nc3cnccn3)cc2CN2CCCC2=O)cn1] | $C_{21}H_{21}N_5O_4S$ | 439 | 1-(2-(6-(methylsulfonyl) pyridin-3-yloxy)-5-(pyrazin-2-ylamino)benzyl) pyrrolidin-2-one | 440 |
| 10 | 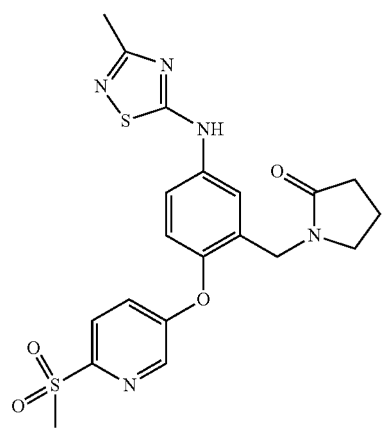 [SMILES: Cc1nsc(Nc2ccc(Oc3ccc(S(C)(=O)=O)nc3)c(CN3CCCC3=O)c2)n1] | $C_{20}H_{21}N_5O_4S_2$ | 460 | 1-(5-(3-methyl-1,2,4-thiadiazol-5-ylamino)-2-(6-(methylsulfonyl) pyridin-3-yloxy)benzyl) pyrrolidin-2-one | 461 |
| 11 | 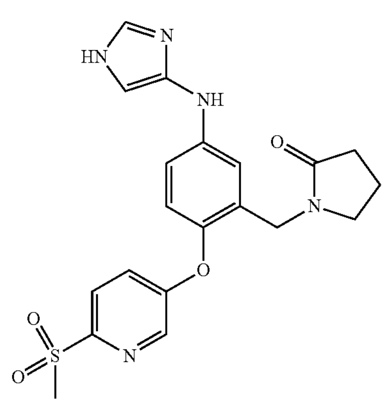 [SMILES: CS(=O)(=O)c1ccc(Oc2ccc(Nc3c[nH]cn3)cc2CN2CCCC2=O)cn1] | $C_{20}H_{21}N_5O_4S$ | 427 | 1-(5-(1H-imidazol-4-ylamino)-2-(6-(methylsulfonyl) pyridin-3-yloxy) benzyl)pyrrolidin-2-one | 428 |

TABLE I-continued

| Example | Structure | Molecular Formula | Molecular Weight | Molecular Name | LC-MS [M + H](m/z) |
|---|---|---|---|---|---|
| 12 | 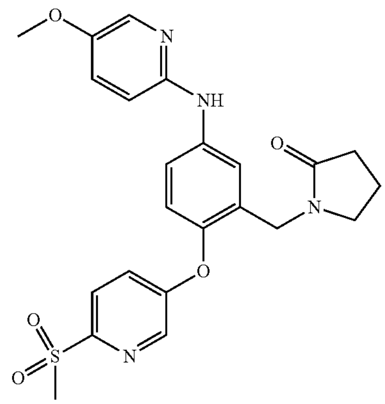 [SMILES: COc1ccc(Nc2ccc(Oc3ccc(S(C)(=O)=O)nc3)c(CN3CCCC3=O)c2)nc1] | C$_{23}$H$_{24}$N$_4$O$_5$S | 469 | 1-(5-(5-methoxypyridin-2-ylamino)-2-(6-(methylsulfonyl)pyridin-3-yloxy)benzyl)pyrrolidin-2-one | 470 |
| 13 | 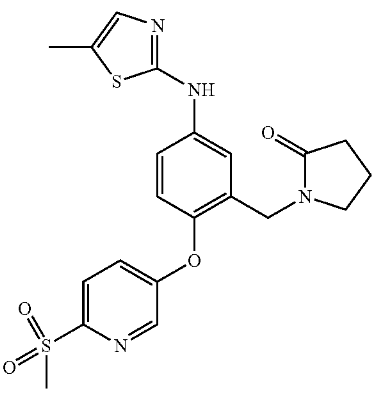 [SMILES: Cc1cnc(Nc2ccc(Oc3ccc(S(C)(=O)=O)nc3)c(CN3CCCC3=O)c2)s1] | C$_{21}$H$_{22}$N$_4$O$_4$S$_2$ | 459 | 1-(2-(6-(methylsulfonyl)pyridin-3-yloxy)-5-(5-methylthiazol-2-ylamino)benzyl)pyrrolidin-2-one | 460 |
| 14 | 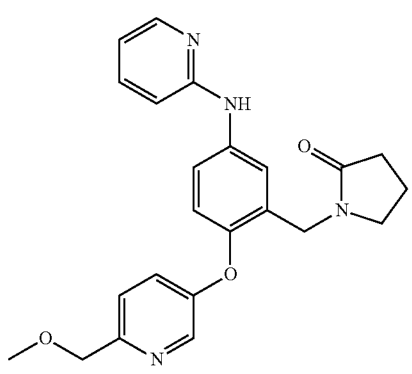 [SMILES: COCc1ccc(Oc2ccc(Nc3ccccn3)cc2CN2CCCC2=O)cn1] | C$_{23}$H$_{24}$N$_4$O$_3$ | 404 | 1-(2-(6-(methoxymethyl)pyridin-3-yloxy)-5-(pyridin-2-ylamino)benzyl)pyrrolidin-2-one | 405 |

TABLE I-continued

| Example | Structure | Molecular Formula | Molecular Weight | Molecular Name | LC-MS [M + H](m/z) |
|---|---|---|---|---|---|
| 15 | 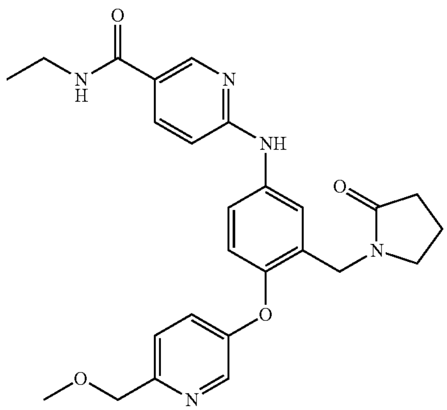 [SMILES: CCNC(=O)c1ccc(Nc2ccc(Oc3ccc(COC)nc3)c(CN3CCCC3=O)c2)nc1] | C<sub>26</sub>H<sub>29</sub>N<sub>5</sub>O<sub>4</sub> | 476 | N-ethyl-6-(4-(6-(methoxymethyl)pyridin-3-yloxy)-3-((2-oxopyrrolidin-1-yl)methyl)phenylamino)nicotinamide | 477 |
| 16 | 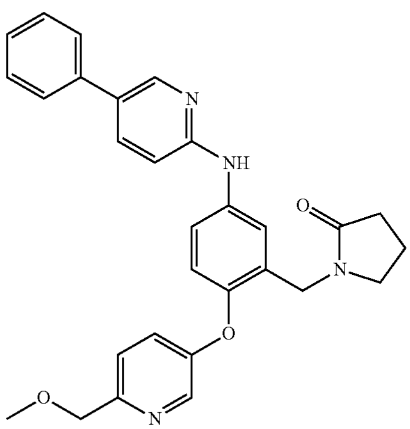 [SMILES: COCc1ccc(Oc2ccc(Nc3ccc(-c4ccccc4)cn3)cc2CN2CCCC2=O)cn1] | C<sub>29</sub>H<sub>28</sub>N<sub>4</sub>O<sub>3</sub> | 481 | 1-(2-(6-(methoxymethyl)pyridin-3-yloxy)-5-(5-phenylpyridin-2-ylamino)benzyl)pyrrolidin-2-one | 482 |
| 17 | 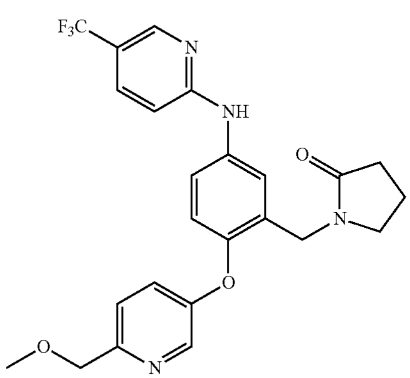 [SMILES: COCc1ccc(Oc2ccc(Nc3ccc(C#N)cn3)cc2CN2CCCC2=O)cn1] | C<sub>24</sub>H<sub>23</sub>F<sub>3</sub>N<sub>4</sub>O<sub>3</sub> | 472 | 1-(2-(6-(methoxymethyl)pyridin-3-yloxy)-5-(5-(trifluoromethyl)pyridin-2-ylamino)benzyl)pyrrolidin-2-one | 473 |

TABLE I-continued

| Example | Molecular Formula | Molecular Weight | Molecular Name | LC-MS [M + H](m/z) |
|---|---|---|---|---|
| 18 | $C_{24}H_{23}N_5O_3$ | 429 | 6-(4-(6-(methoxymethyl) pyridin-3-yloxy)-3-((2-oxopyrrolidin-1-yl)methyl) phenylamino) nicotinonitrile | 430 |
| 19 | $C_{24}H_{24}N_4O_5$ | 448 | 6-(4-(6-(methoxymethyl) pyridin-3-yloxy)-3-((2-oxopyrrolidin-1-yl)methyl) phenylamino) nicotinic acid | 449 |
| 20 | $C_{26}H_{28}N_4O_5$ | 477 | ethyl 6-(4-(6-(methoxymethyl) pyridin-3-yloxy)-3-((2-oxopyrrolidin-1-yl)methyl) phenylamino) nicotinate | 478 |
| 21 | $C_{24}H_{26}N_4O_3$ | 418 | 1-(2-(6-(methoxymethyl) pyridin-3-yloxy)-5-(5-methylpyridin-2-ylamino) benzyl)pyrrolidin-2-one | 419 |

TABLE I-continued

| Example | Structure | Molecular Formula | Molecular Weight | Molecular Name | LC-MS [M + H](m/z) |
|---|---|---|---|---|---|
| 22 | 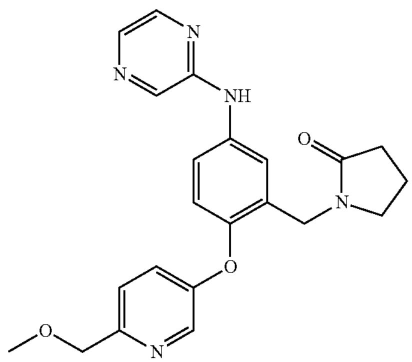 [SMILES: COCc1ccc(Oc2ccc(Nc3cnccn3)cc2CN2CCCC2=O)cn1] | $C_{22}H_{23}N_5O_3$ | 405 | 1-(2-(6-(methoxymethyl) pyridin-3-yloxy)-5-(pyrazin-2-ylamino)benzyl) pyrrolidin-2-one | 406 |
| 23 | 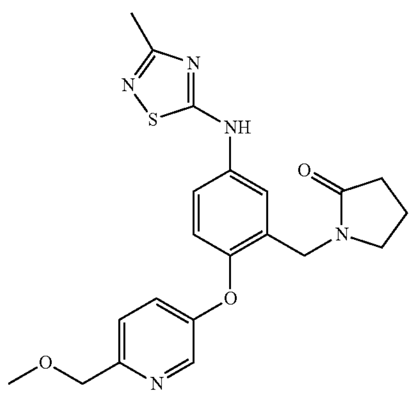 [SMILES: COCc1ccc(Oc2ccc(Nc3nc(C)ns3)cc2CN2CCCC2=O)cn1] | $C_{21}H_{23}N_5O_3S$ | 426 | 1-(2-(6-(methoxymethyl) pyridin-3-yloxy)-5-(3-methyl-1,2,4-thiadiazol-5-ylamino)benzyl) pyrrolidin-2-one | 427 |
| 24 | 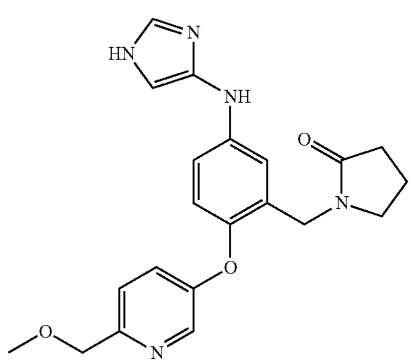 [SMILES: COCc1ccc(Oc2ccc(Nc3c[nH]cn3)cc2CN2CCCC2=O)cn1] | $C_{21}H_{23}N_5O_3$ | 393 | 1-(5-(1H-imidazol-4-ylamino)-2-(6-(methoxymethyl)pyridin-3-yloxy) benzyl)pyrrolidin-2-one | 394 |
| 25 | 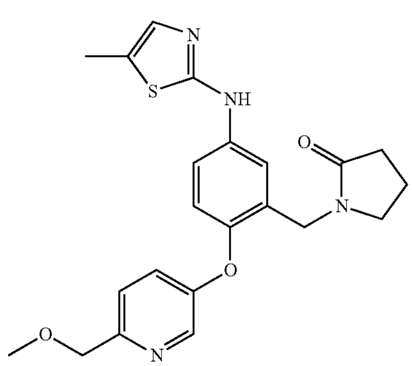 [SMILES: COCc1ccc(Oc2ccc(Nc3ncc(C)s3)cc2CN2CCCC2=O)cn1] | $C_{22}H_{24}N_4O_3S$ | 425 | 1-(2-(6-(methoxymethyl) pyridin-3-yloxy)-5-(5-methylthiazol-2-ylamino) benzyl)pyrrolidin-2-one | 426 |

TABLE I-continued

| Example | Structure | Molecular Formula | Molecular Weight | Molecular Name | LC-MS [M+H](m/z) |
|---|---|---|---|---|---|
| 26 | 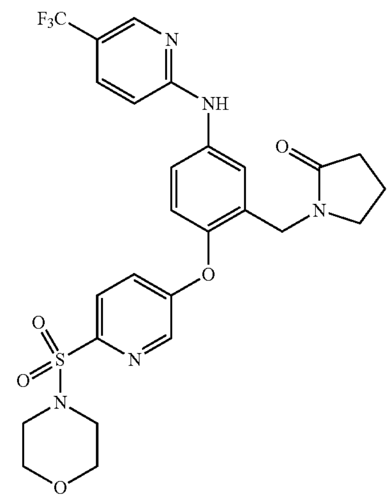 [SMILES: O=C1CCCN1Cc1cc(Nc2ccc(C(F)(F)F)cn2)ccc1Oc1ccc(S(=O)(=O)N2CCOCC2)nc1] | C₂₆H₂₆F₃N₅O₅S | 425 | 1-(2-(6-(morpholinosulfonyl)pyridin-3-yloxy)-5-(5-(trifluoromethyl)pyridin-2-ylamino)benzyl)pyrrolidin-2-one | 426 |
| 27 | 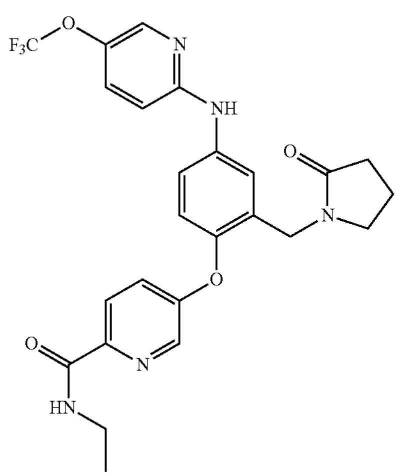 [SMILES: CCNC(=O)c1ccc(Oc2ccc(Nc3ccc(OC(F)(F)F)cn3)cc2CN2CCCC2=O)cn1] | C₂₅H₂₄F₃N₅O₄ | 515 | N-ethyl-5-(2-((2-oxopyrrolidin-1-yl)methyl)-4-(5-(trifluoromethoxy)pyridin-2-ylamino)phenoxy)picolinamide | 516 |
| 28 | 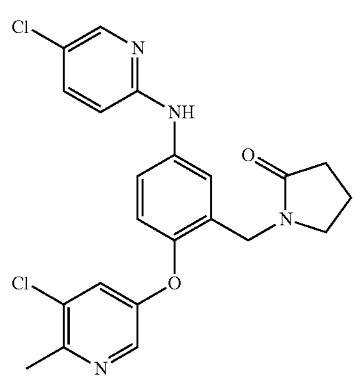 [SMILES: Cc1ncc(Oc2ccc(Nc3ccc(Cl)cn3)cc2CN2CCCC2=O)cc1Cl] | C₂₂H₂₀Cl₂N₄O₂ | 443 | 1-(2-(5-chloro-6-methylpyridin-3-yloxy)-5-(5-chloropyridin-2-ylamino)benzyl)pyrrolidin-2-one | 444 |

TABLE I-continued
| Example | Structure | Molecular Formula | Molecular Weight | Molecular Name | LC-MS [M + H](m/z) |
|---|---|---|---|---|---|
| 29 | 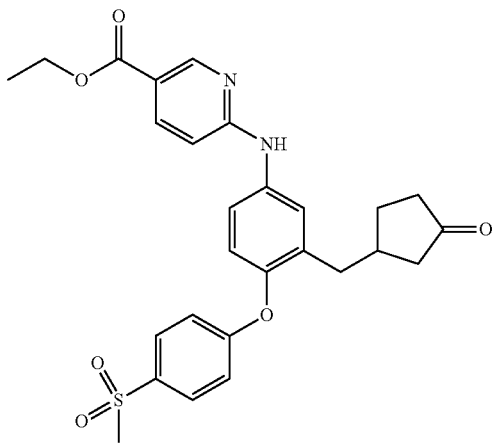 [SMILES: CCOC(=O)c1ccc(Nc2ccc(Oc3ccc(S(C)(=O)=O)cc3)c(CC3CCC(=O)C3)c2)nc1] | $C_{27}H_{28}N_2O_6S$ | 509 | ethyl 6-(4-(4-(methylsulfonyl)phenoxy)-3-((3-oxocyclopentyl)methyl)phenylamino)nicotinate | 510 |
| 30 | 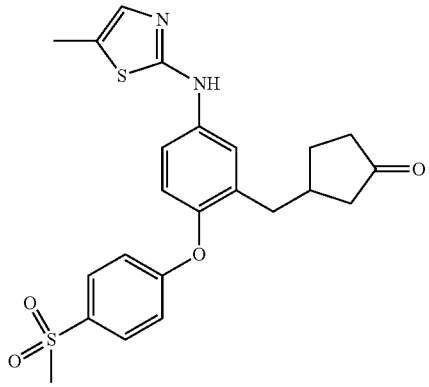 [SMILES: Cc1cnc(Nc2ccc(Oc3ccc(S(C)(=O)=O)cc3)c(CC3CCC(=O)C3)c2)s1] | $C_{23}H_{24}N_2O_4S_2$ | 457 | 3-(2-(4-(methylsulfonyl)phenoxy)-5-(5-methylthiazol-2-ylamino)benzyl)cyclopentanone | 458 |
| 31 | 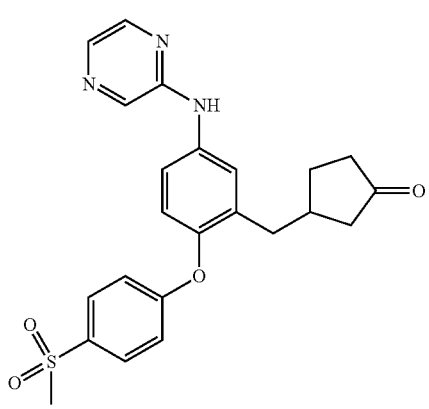 [SMILES: CS(=O)(=O)c1ccc(Oc2ccc(Nc3cnccn3)cc2CC2CCC(=O)C2)cc1] | $C_{23}H_{23}N_3O_4S$ | 438 | 3-(2-(4-(methylsulfonyl)phenoxy)-5-(pyrazin-2-ylamino)benzyl)cyclopentanone | 439 |

TABLE I-continued

| Example | Structure | Molecular Formula | Molecular Weight | Molecular Name | LC-MS [M + H](m/z) |
|---|---|---|---|---|---|
| 32 | 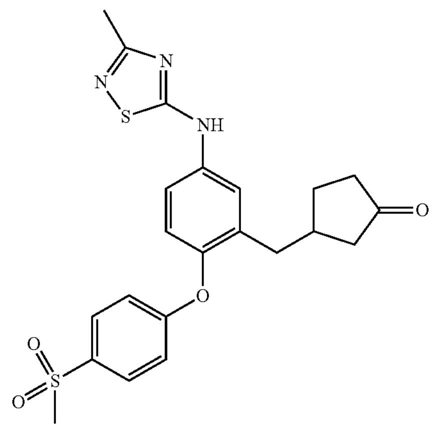 [SMILES: Cc1nsc(Nc2ccc(Oc3ccc(S(C)(=O)=O)cc3)c(CC3CCC(=O)C3)c2)n1] | $C_{22}H_{23}N_3O_4S_2$ | 458 | 3-(5-(3-methyl-1,2,4-thiadiazol-5-ylamino)-2-(4-(methylsulfonyl) phenoxy)benzyl) cyclopentanone | 459 |
| 33 | 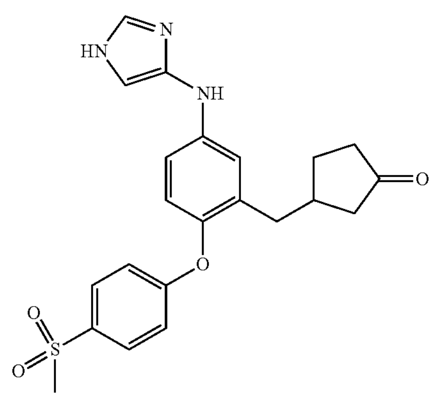 [SMILES: CS(=O)(=O)c1ccc(Oc2ccc(Nc3c[nH]cn3)cc2CC2CCC(=O)C2)cc1] | $C_{22}H_{23}N_3O_4S$ | 426 | 3-(5-(1H-imidazol-4-yl amino)-2-(4-(methylsulfonyl) phenoxy)benzyl) cyclopentanone | 427 |
| 34 | 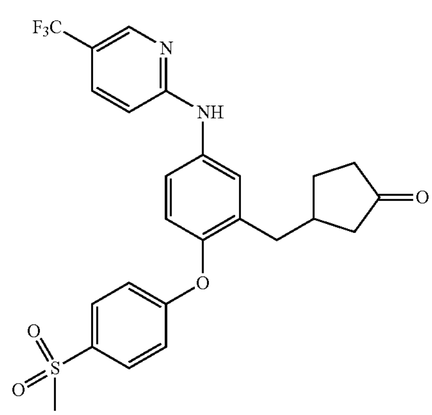 [SMILES: CS(=O)(=O)c1ccc(Oc2ccc(Nc3ccc(C(F)(F)F)cn3)cc2CC2CCC(=O)C2)cc1] | $C_{25}H_{23}F_3N_2O_4S$ | 505 | 3-(2-(4-(methylsulfonyl) phenoxy)-5-(5-(trifluoromethyl) pyridin-2-ylamino) benzyl) cyclopentanone | 506 |

TABLE I-continued

| Example | Structure | Molecular Formula | Molecular Weight | Molecular Name | LC-MS [M + H](m/z) |
|---------|-----------|-------------------|------------------|----------------|---------------------|
| 36 | 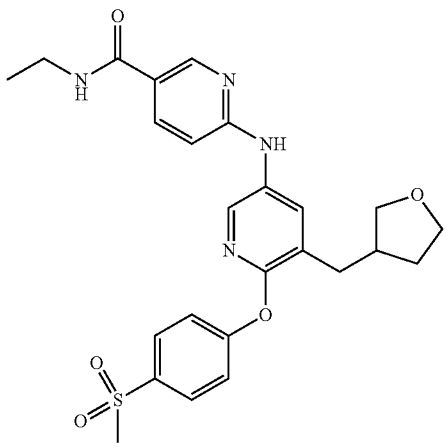 [SMILES: CCNC(=O)c1ccc(Nc2cnc(Oc3ccc(S(C)(=O)=O)cc3)c(CC3CCOC3)c2)nc1] | $C_{25}H_{28}N_4O_5S$ | 497 | N-ethyl-6-(6-(4-(methylsulfonyl)phenoxy)-5-((tetrahydrofuran-3-yl)methyl)pyridin-3-ylamino)nicotinamide | 498 |
| 37 | 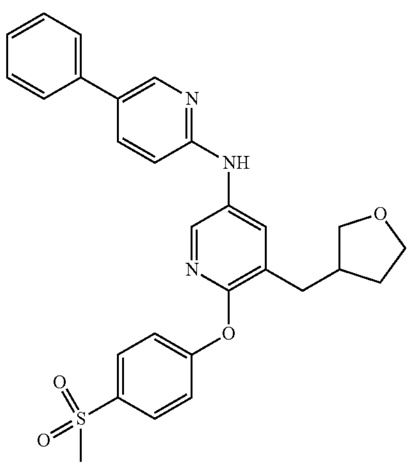 [SMILES: CS(=O)(=O)c1ccc(Oc2ncc(Nc3ccc(-c4ccccc4)cn3)cc2CC2CCOC2)cc1] | $C_{28}H_{27}N_3O_4S$ | 502 | N-(6-(4-(methylsulfonyl)phenoxy)-5-((tetrahydrofuran-3-yl)methyl)pyridin-3-yl)-5-phenylpyridin-2-amine | 503 |
| 38 | 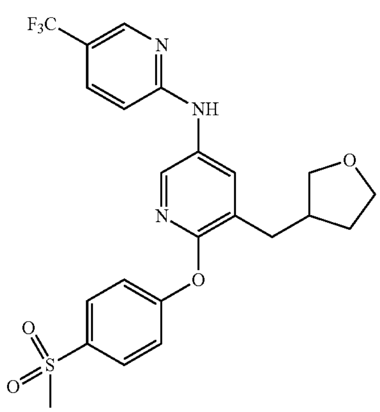 | $C_{23}H_{22}F_3N_3O_4S$ | 493 | N-(6-(4-(methylsulfonyl)phenoxy)-5-((tetrahydrofuran-3-yl)methyl)pyridin-3-yl)-5-(trifluoromethyl)pyridin-2-amine | 494 |

TABLE I-continued

| Example | Structure | Molecular Formula | Molecular Weight | Molecular Name | LC-MS [M + H](m/z) |
|---|---|---|---|---|---|
| 39 | 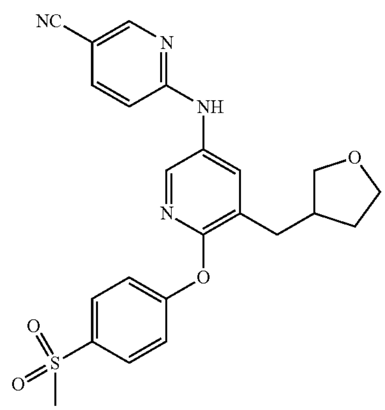 [SMILES: CS(=O)(=O)c1ccc(Oc2ncc(Nc3ccc(C#N)cn3)cc2CC2CCOC2)cc1] | $C_{23}H_{22}N_4O_4S$ | 451 | 6-(6-(4-(methylsulfonyl)phenoxy)-5-((tetrahydrofuran-3-yl)methyl)pyridin-3-ylamino)nicotinonitrile | 452 |
| 40 | 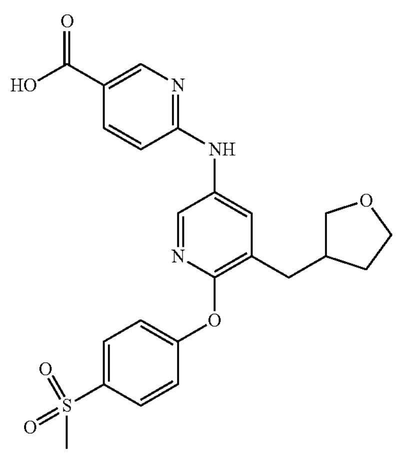 [SMILES: CS(=O)(=O)c1ccc(Oc2ncc(Nc3ccc(C(=O)O)cn3)cc2CC2CCOC2)cc1] | $C_{23}H_{23}N_3O_6S$ | 407 | 6-(6-(4-(methylsulfonyl)phenoxy)-5-((tetrahydrofuran-3-yl)methyl)pyridin-3-ylamino)nicotinic acid | 471 |
| 41 | 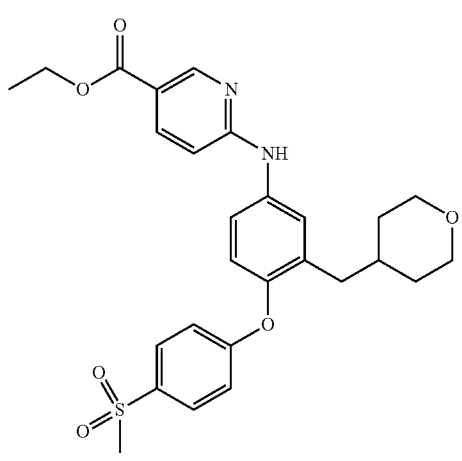 [SMILES: CCOC(=O)c1ccc(Nc2ccc(Oc3ccc(S(C)(=O)=O)cc3)c(CC3CCOCC3)c2)nc1] | $C_{27}H_{30}N_2O_6S$ | 511 | ethyl 6-(4-(4-(methylsulfonyl)phenoxy)-3-((tetrahydro-2H-pyran-4-yl)methyl)phenylamino)nicotinate | 512 |

TABLE I-continued

| Example | Structure | Molecular Formula | Molecular Weight | Molecular Name | LC-MS [M + H](m/z) |
| --- | --- | --- | --- | --- | --- |
| 42 | 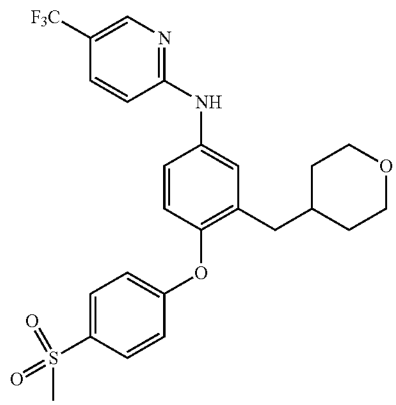 [SMILES: CS(=O)(=O)c1ccc(Oc2ccc(Nc3ccc(C(F)(F)F)cn3)cc2CC2CCOCC2)cc1] | $C_{25}H_{25}F_3N_2O_4S$ | 507 | N-(4-(4-(methylsulfonyl)phenoxy)-3-((tetrahydro-2H-pyran-4-yl)methyl)phenyl)-5-(trifluoromethyl)pyridin-2-amine | 508 |
| 43 | 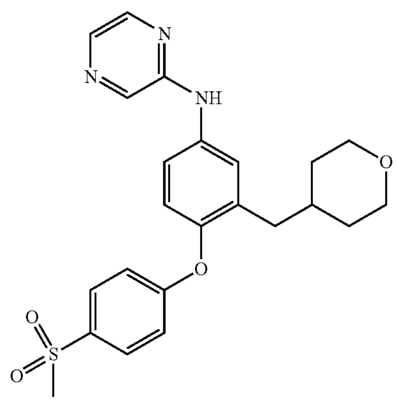 [SMILES: CS(=O)(=O)c1ccc(Oc2ccc(Nc3cnccn3)cc2CC2CCOCC2)cc1] | $C_{23}H_{25}N_3O_4S$ | 440 | N-(4-(4-(methylsulfonyl)phenoxy)-3-((tetrahydro-2H-pyran-4-yl)methyl)phenyl)pyrazin-2-amine | 441 |
| 44 | 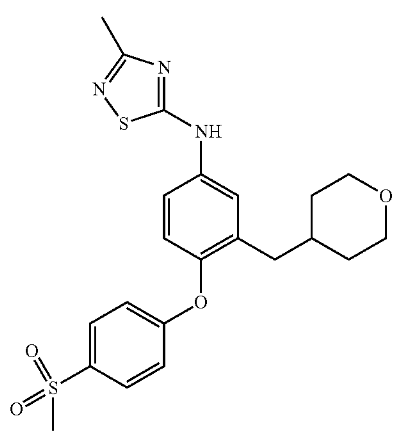 [SMILES: Cc1nsc(Nc2ccc(Oc3ccc(S(C)(=O)=O)cc3)c(CC3CCOCC3)c2)n1] | $C_{22}H_{25}N_3O_4S_2$ | 460 | 3-methyl-N-(4-(4-(methylsulfonyl)phenoxy)-3-((tetrahydro-2H-pyran-4-yl)methyl)phenyl)-1,2,4-thiadiazol-5-amine | 461 |

TABLE I-continued

| Example | Structure | Molecular Formula | Molecular Weight | Molecular Name | LC-MS [M + H](m/z) |
|---|---|---|---|---|---|
| 45 | 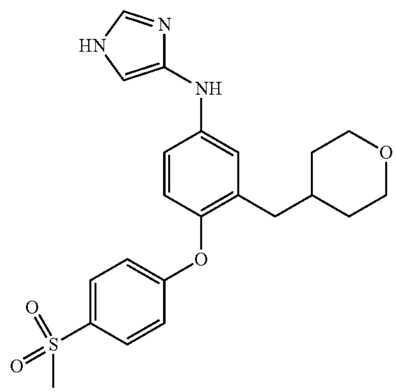 [SMILES: CS(=O)(=O)c1ccc(Oc2ccc(Nc3c[nH]cn3)cc2CC2CCOCC2)cc1] | C₂₂H₂₅N₃O₄S | 428 | N-(4-(4-(methylsulfonyl)phenoxy)-3-((tetrahydro-2H-pyran-4-yl)methyl)phenyl)-1H-imidazol-4-amine | 429 |
| 46 | 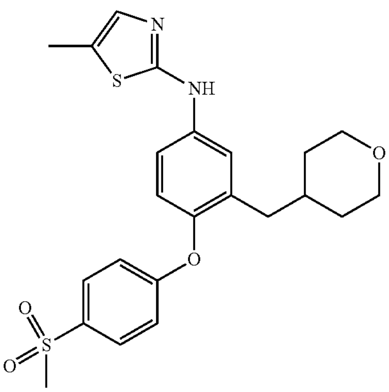 [SMILES: Cc1cnc(Nc2ccc(Oc3ccc(S(C)(=O)=O)cc3)c(CC3CCOCC3)c2)s1] | C₂₃H₂₆N₂O₄S₂ | 459 | 5-methyl-N-(4-(4-(methylsulfonyl)phenoxy)-3-((tetrahydro-2H-pyran-4-yl)methyl)phenyl)thiazol-2-amine | 460 |
| 47 | 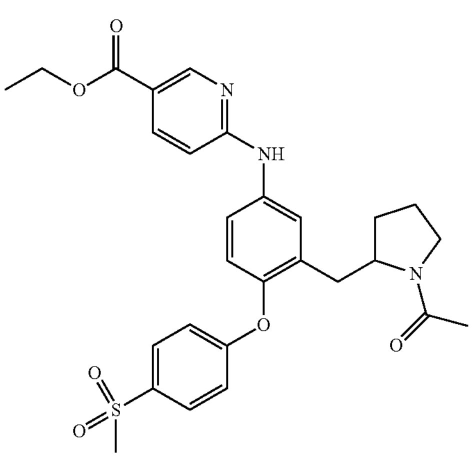 [SMILES: CCOC(=O)c1ccc(Nc2ccc(Oc3ccc(S(C)(=O)=O)cc3)c(CC3CCCN3C(C)=O)c2)nc1] | C₂₈H₃₁N₃O₆S | 538 | ethyl 6-(3-((1-acetylpyrrolidin-2-yl)methyl)-4-(4-(methylsulfonyl)phenoxy)phenylamino)nicotinate | 539 |

TABLE I-continued

| Example | Structure | Molecular Formula | Molecular Weight | Molecular Name | LC-MS [M + H](m/z) |
|---|---|---|---|---|---|
| 48 | 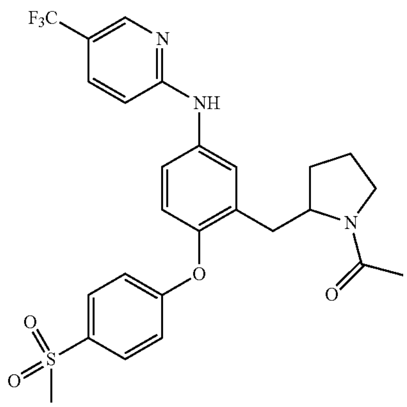 [SMILES: CC(=O)N1CCCC1Cc1cc(Nc2ccc(C(F)(F)F)cn2)ccc1Oc1ccc(S(C)(=O)=O)cc1] | $C_{26}H_{26}F_3N_3O_4S$ | 534 | 1-(2-(2-(4-(methylsulfonyl)phenoxy)-5-(5-(trifluoromethyl)pyridin-2-ylamino)benzyl)pyrrolidin-1-yl)ethanone | 535 |
| 49 | 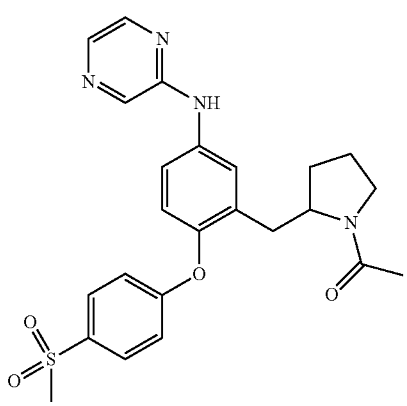 [SMILES: CC(=O)N1CCCC1Cc1cc(Nc2cnccn2)ccc1Oc1ccc(S(C)(=O)=O)cc1] | $C_{24}H_{26}N_4O_4S$ | 467 | 1-(2-(2-(4-(methylsulfonyl)phenoxy)-5-(pyrazin-2-ylamino)benzyl)pyrrolidin-1-yl)ethanone | 468 |
| 50 | 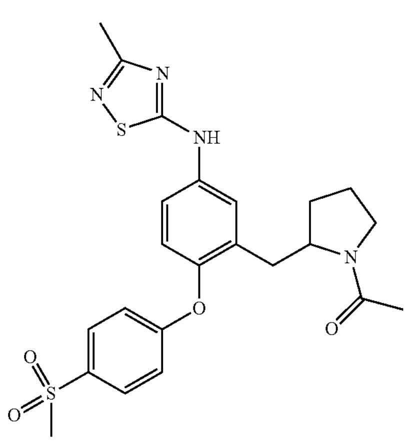 [SMILES: CC(=O)N1CCCC1Cc1cc(Nc2nc(C)ns2)ccc1Oc1ccc(S(C)(=O)=O)cc1] | $C_{23}H_{26}N_4O_4S_2$ | 487 | 1-(2-(5-(3-methyl-1,2,4-thiadiazol-5-ylamino)-2-(4-(methylsulfonyl)phenoxy)benzyl)pyrrolidin-1-yl)ethanone | 488 |

TABLE I-continued

| Example | Structure | Molecular Formula | Molecular Weight | Molecular Name | LC-MS [M + H](m/z) |
|---|---|---|---|---|---|
| 51 | 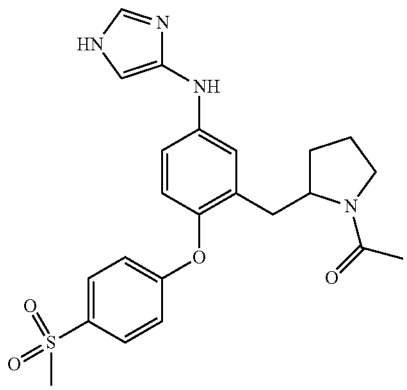 [SMILES: CC(=O)N1CCCC1Cc1cc(Nc2c[nH]cn2)ccc1Oc1ccc(S(C)(=O)=O)cc1] | C₂₃H₂₆N₄O₄S | 455 | 1-(2-(5-(1H-imidazol-4-ylamino)-2-(4-(methylsulfonyl)phenoxy)benzyl)pyrrolidin-1-yl)ethanone | 456 |
| 52 | 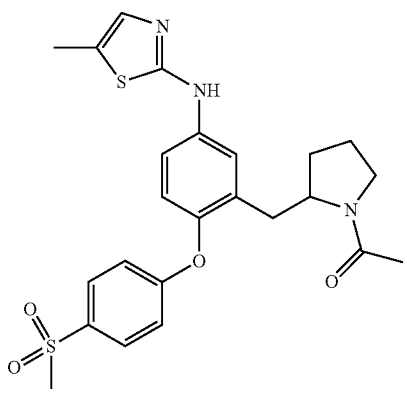 [SMILES: CC(=O)N1CCCC1Cc1cc(Nc2ncc(C)s2)ccc1Oc1ccc(S(C)(=O)=O)cc1] | C₂₄H₂₇N₃O₄S₂ | 486 | 1-(2-(2-(4-(methylsulfonyl)phenoxy)-5-(5-methylthiazol-2-ylamino)benzyl)pyrrolidin-1-yl)ethanone | 487 |
| 54 | 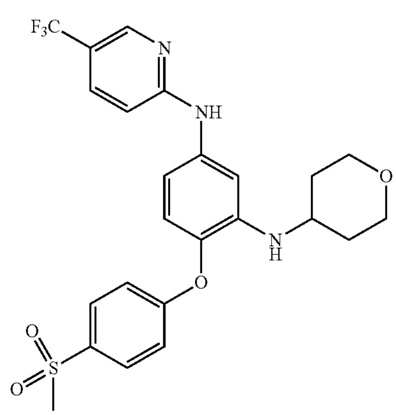 [SMILES: CS(=O)(=O)c1ccc(Oc2ccc(Nc3ccc(C(F)(F)F)cn3)cc2NC2CCOCC2)cc1] | C₂₄H₂₄F₃N₃O₄S | 508 | 4-(4-(methylsulfonyl)phenoxy)-N3-(tetrahydro-2H-pyran-4-yl)-N1-(5-(trifluoromethyl)pyridin-2-yl)benzene-1,3-diamine | 509 |

TABLE I-continued

| Example | Structure | Molecular Formula | Molecular Weight | Molecular Name | LC-MS [M + H](m/z) |
|---------|-----------|-------------------|------------------|----------------|--------------------|
| 55 | 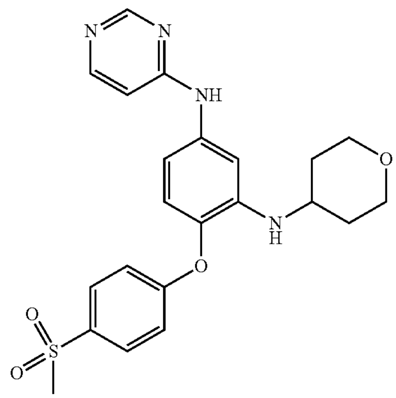 [SMILES: CS(=O)(=O)c1ccc(Oc2ccc(Nc3ccncn3)cc2NC2CCOCC2)cc1] | C₂₂H₂₄N₄O₄S | 441 | 4-(4-(methylsulfonyl)phenoxy)-N1-(pyrimidin-4-yl)-N3-(tetrahydro-2H-pyran-4-yl)benzene-1,3-diamine | 442 |
| 57 | 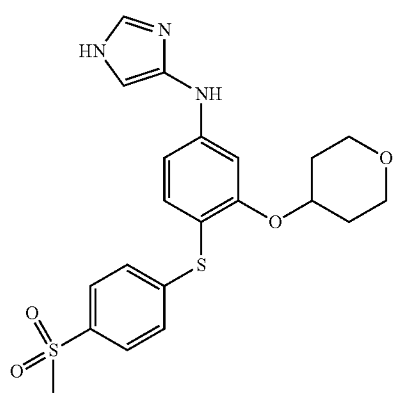 [SMILES: CS(=O)(=O)c1ccc(Sc2ccc(Nc3c[nH]cn3)cc2OC2CCOCC2)cc1] | C₂₁H₂₃N₃O₄S₂ | 446 | N-(4-(4-(methylsulfonyl)phenylthio)-3-(tetrahydro-2H-pyran-4-yloxy)phenyl)-1H-imidazol-4-amine | 447 |
| 58 | 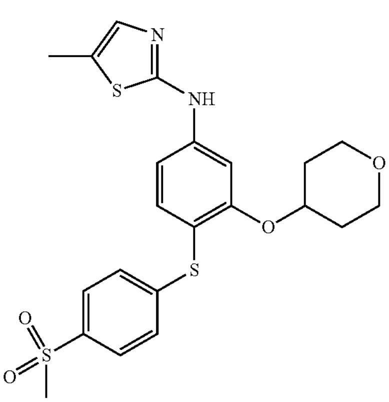 [SMILES: Cc1cnc(Nc2ccc(Sc3ccc(S(C)(=O)=O)cc3)c(OC3CCOCC3)c2)s1] | C₂₂H₂₄N₂O₄S₃ | 477 | 5-methyl-N-(4-(4-(methylsulfonyl)phenylthio)-3-(tetrahydro-2H-pyran-4-yloxy)phenyl)thiazol-2-amine | 478 |

TABLE I-continued

| Example | Structure | Molecular Formula | Molecular Weight | Molecular Name | LC-MS [M + H](m/z) |
|---|---|---|---|---|---|
| 59 | 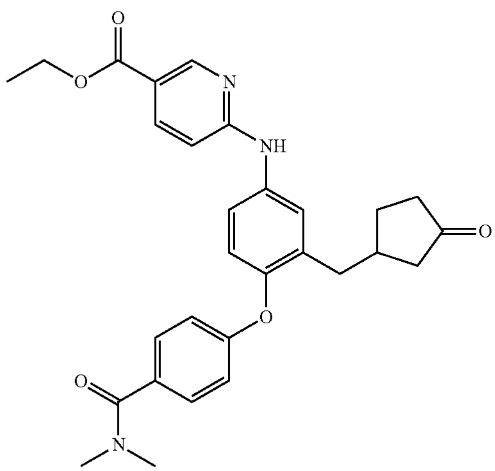 [SMILES: CCOC(=O)c1ccc(Nc2ccc(Oc3ccc(C(=O)N(C)C)cc3)c(CC3CCC(=O)C3)c2)nc1] | $C_{29}H_{31}N_3O_5$ | 502 | ethyl 6-(4-(4-(dimethylcarbamoyl)phenoxy)-3-((3-oxocyclopentyl)methyl)phenylamino)nicotinate | 503 |
| 60 | 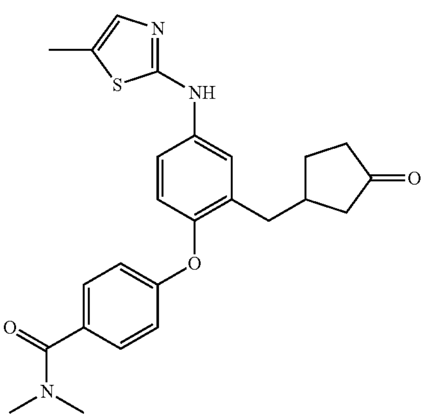 [SMILES: Cc1cnc(Nc2ccc(Oc3ccc(C(=O)N(C)C)cc3)c(CC3CCC(=O)C3)c2)s1] | $C_{25}H_{27}N_3O_3S$ | 450 | N,N-dimethyl-4-(4-(5-methylthiazol-2-ylamino)-2-((3-oxocyclopentyl)methyl)phenoxy)benzamide | 451 |
| 61 | 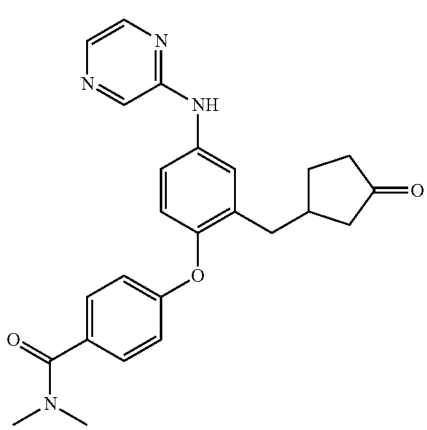 [SMILES: CN(C)C(=O)c1ccc(Oc2ccc(Nc3cnccn3)cc2CC2CCC(=O)C2)cc1] | $C_{25}H_{26}N_4O_3$ | 430 | N,N-dimethyl-4-(2-((3-oxocyclopentyl)methyl)-4-(pyrazin-2-ylamino)phenoxy)benzamide | 431 |

TABLE I-continued

| Example | Structure | Molecular Formula | Molecular Weight | Molecular Name | LC-MS [M + H](m/z) |
|---|---|---|---|---|---|
| 62 | 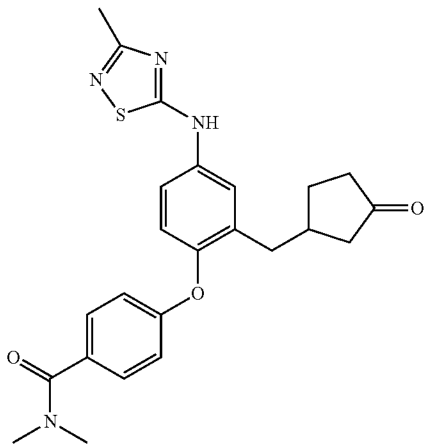 [SMILES: Cc1nsc(Nc2ccc(Oc3ccc(C(=O)N(C)C)cc3)c(CC3CCC(=O)C3)c2)n1] | C₂₄H₂₆N₄O₃S | 451 | N,N-dimethyl-4-(4-(3-methyl-1,2,4-thiadiazol-5-ylamino)-2-((3-oxocyclopentyl)methyl)phenoxy)benzamide | 452 |
| 63 | 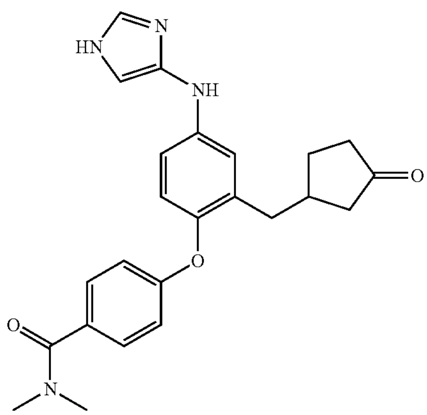 [SMILES: CN(C)C(=O)c1ccc(Oc2ccc(Nc3c[nH]cn3)cc2CC2CCC(=O)C2)cc1] | C₂₄H₂₆N₄O₃ | 418 | 4-(4-(1H-imidazol-4-ylamino)-2-((3-oxocyclopentyl)methyl)phenoxy)-N,N-dimethylbenzamide | 419 |
| 64 | 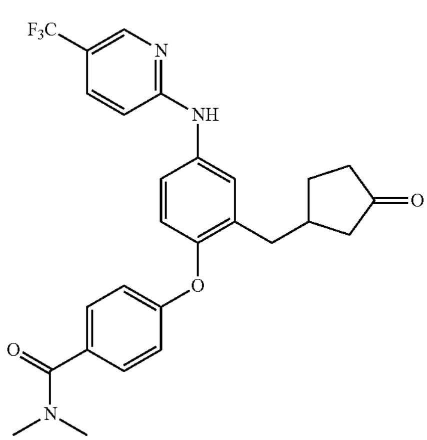 [SMILES: CN(C)C(=O)c1ccc(Oc2ccc(Nc3ccc(C(F)(F)F)cn3)cc2CC2CCC(=O)C2)cc1] | C₂₇H₂₆F₃N₃O₃ | 498 | N,N-dimethyl-4-(2-((3-oxocyclopentyl)methyl)-4-(5-(trifluoromethyl)pyridin-2-ylamino)phenoxy)benzamide | 499 |

TABLE I-continued

| Example | Structure | Molecular Formula | Molecular Weight | Molecular Name | LC-MS [M + H](m/z) |
|---|---|---|---|---|---|
| 66 | 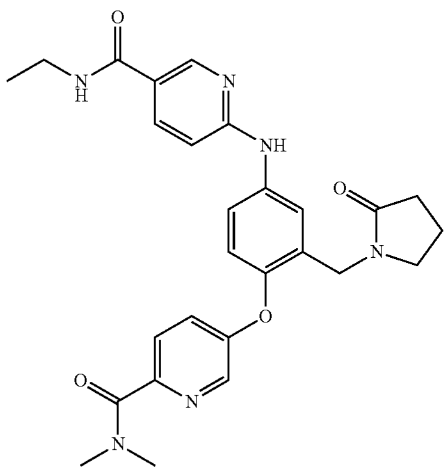 [SMILES: CCNC(=O)c1ccc(Nc2ccc(Oc3ccc(C(=O)N(C)C)nc3)c(CN3CCCC3=O)c2)nc1] | C₂₇H₃₀N₆O₄ | 503 | 5-(4-(5-(ethylcarbamoyl) pyridin-2-ylamino)-2-((2-oxopyrrolidin-1-yl) methyl)phenoxy)-N,N-dimethylpicolinamide | 504 |
| 67 | 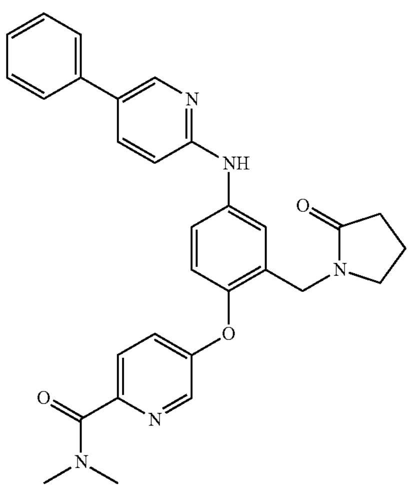 [SMILES: CN(C)C(=O)c1ccc(Oc2ccc(Nc3ccc(-c4ccccc4)cn3)cc2CN2CCCC2=O)cn1] | C₃₀H₂₉N₅O₃ | 508 | N,N-dimethyl-5-(2-((2-oxopyrrolidin-1-yl) methyl)-4-(5-phenylpyridin-2-ylamino)phenoxy) picolinamide | 509 |
| 68 | 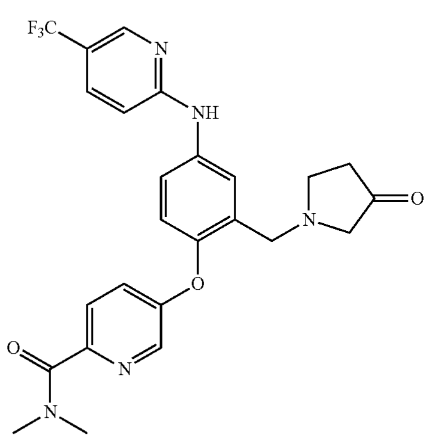 [SMILES: CN(C)C(=O)c1ccc(Oc2ccc(Nc3ccc(C(F)(F)F)cn3)cc2CN2CCC(=O)C2)cn1] | C₂₅H₂₄F₃N₅O₃ | 499 | N,N-dimethyl-5-(2-((2-oxopyrrolidin-1-yl) methyl)-4-(5-(trifluoromethyl) pyridin-2-ylamino) phenoxy)picolinamide | 500 |

TABLE I-continued

| Example | Structure | Molecular Formula | Molecular Weight | Molecular Name | LC-MS [M + H](m/z) |
|---------|-----------|-------------------|------------------|----------------|---------------------|
| 69 | 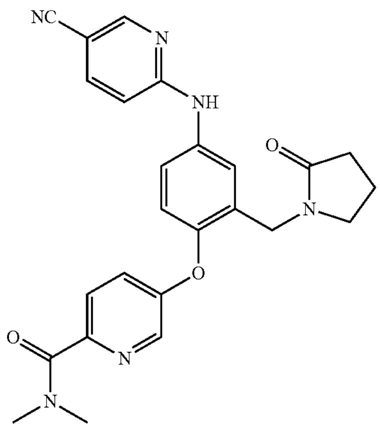 [SMILES: CN(C)C(=O)c1ccc(Oc2ccc(Nc3ccc(C#N)cn3)cc2CN2CCCC2=O)cn1] | C₂₅H₂₄N₆O₃ | 456 | 5-(4-(5-cyanopyridin-2-ylamino)-2-((2-oxopyrrolidin-1-yl)methyl)phenoxy)-N,N-dimethylpicolinamide | 457 |
| 70 | 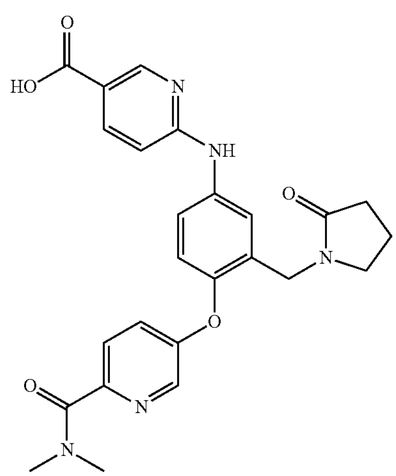 [SMILES: CN(C)C(=O)c1ccc(Oc2ccc(Nc3ccc(C(=O)O)cn3)cc2CN2CCCC2=O)cn1] | C₂₅H₂₅N₅O₅ | 475 | 6-(4-(6-(dimethylcarbamoyl)pyridin-3-yloxy)-3-((2-oxopyrrolidin-1-yl)methyl)phenylamino)nicotinic acid | 476 |
| 71 | 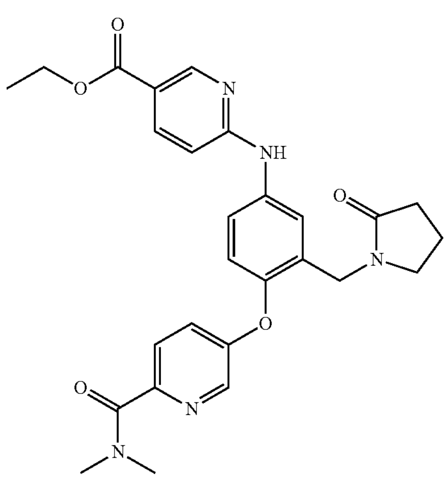 [SMILES: CCOC(=O)c1ccc(Nc2ccc(Oc3ccc(C(=O)N(C)C)nc3)c(CN3CCCC3=O)c2)nc1] | C₂₇H₂₉N₅O₅ | 504 | ethyl 6-(4-(6-(dimethylcarbamoyl)pyridin-3-yloxy)-3-((2-oxopyrrolidin-1-yl)methyl)phenylamino)nicotinate | 505 |

TABLE I-continued

| Example | Structure | Molecular Formula | Molecular Weight | Molecular Name | LC-MS [M + H](m/z) |
|---|---|---|---|---|---|
| 72 | 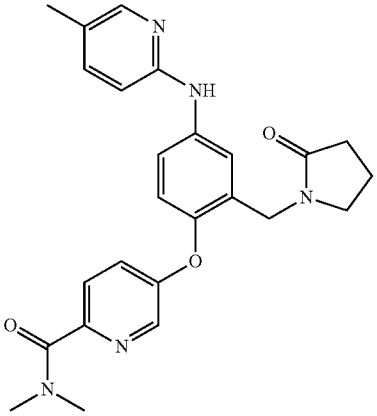 [SMILES: Cc1ccc(Nc2ccc(Oc3ccc(C(=O)N(C)C)nc3)c(CN3CCCC3=O)c2)nc1] | C₂₅H₂₇N₅O₃ | 446 | N,N-dimethyl-5-(4-(5-methylpyridin-2-ylamino)-2-((2-oxopyrrolidin-1-yl)methyl)phenoxy)picolinamide | 447 |
| 73 | 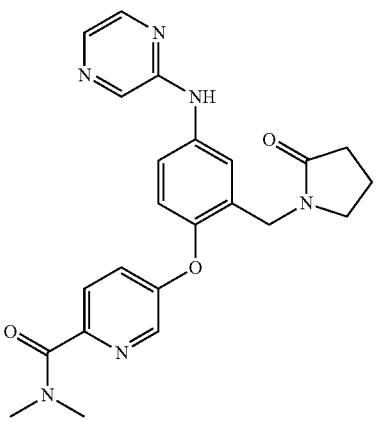 [SMILES: CN(C)C(=O)c1ccc(Oc2ccc(Nc3cnccn3)cc2CN2CCCC2=O)cn1] | C₂₃H₂₄N₆O₃ | 432 | N,N-dimethyl-5-(2-((2-oxopyrrolidin-1-yl)methyl)-4-(pyrazin-2-ylamino)phenoxy)picolinamide | 433 |
| 74 | 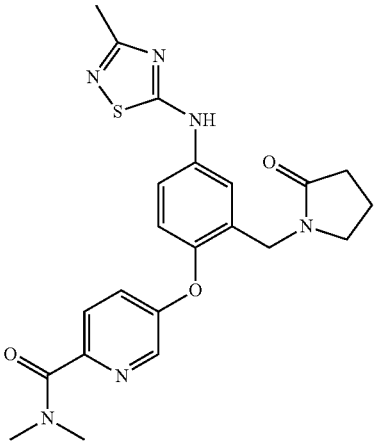 [SMILES: Cc1nsc(Nc2ccc(Oc3ccc(C(=O)N(C)C)nc3)c(CN3CCCC3=O)c2)n1] | C₂₂H₂₄N₆O₃S | 453 | N,N-dimethyl-5-(4-(3-methyl-1,2,4-thiadiazol-5-ylamino)-2-((2-oxopyrrolidin-1-yl)methyl)phenoxy)picolinamide | 454 |

TABLE I-continued

| Example | Structure | Molecular Formula | Molecular Weight | Molecular Name | LC-MS [M + H](m/z) |
|---|---|---|---|---|---|
| 75 | 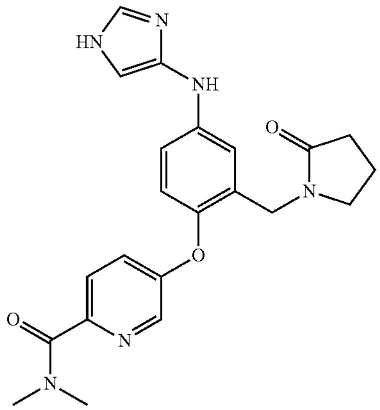 [SMILES: CN(C)C(=O)c1ccc(Oc2ccc(Nc3c[nH]cn3)cc2CN2CCCC2=O)cn1] | C$_{22}$H$_{24}$N$_6$O$_3$ | 420 | 5-(4-(1H-imidazol-4-ylamino)-2-((2-oxopyrrolidin-1-yl)methyl)phenoxy)-N,N-dimethylpicolinamide | 421 |
| 76 | 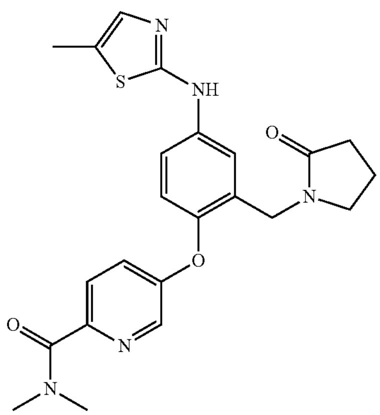 [SMILES: Cc1cnc(Nc2ccc(Oc3ccc(C(=O)N(C)C)nc3)c(CN3CCCC3=O)c2)s1] | C$_{23}$H$_{25}$N$_5$O$_3$S | 452 | N,N-dimethyl-5-(4-(5-methylthiazol-2-ylamino)-2-((2-oxopyrrolidin-1-yl)methyl)phenoxy)picolinamide | 453 |
| 77 | 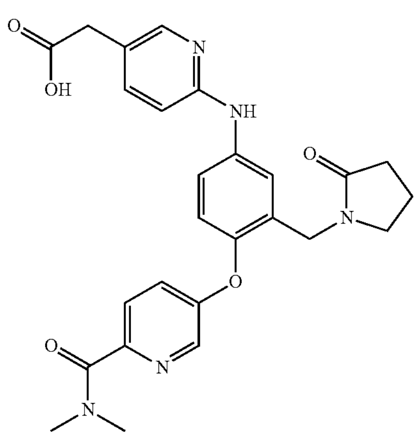 [SMILES: CN(C)C(=O)c1ccc(Oc2ccc(Nc3ccc(CC(=O)O)cn3)cc2CN2CCCC2=O)cn1] | C$_{26}$H$_{27}$N$_5$O$_5$ | 490 | 2-(6-(4-(6-(dimethylcarbamoyl)pyridin-3-yloxy)-3-((2-oxopyrrolidin-1-yl)methyl)phenylamino)pyridin-3-yl)acetic acid | 491 |

TABLE I-continued

| Example | Structure | Molecular Formula | Molecular Weight | Molecular Name | LC-MS [M + H](m/z) |
|---------|-----------|-------------------|------------------|----------------|---------------------|
| 78 | 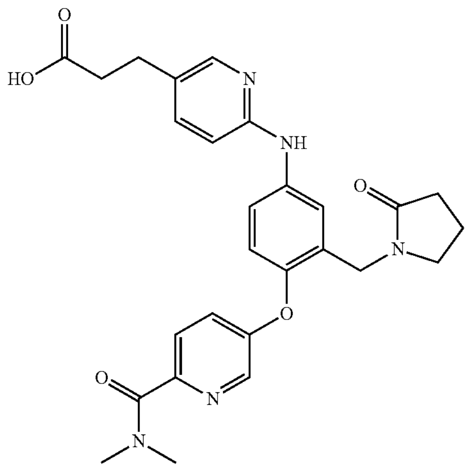 [SMILES: CN(C)C(=O)c1ccc(Oc2ccc(Nc3ccc(CCC(=O)O)cn3)cc2CN2CCCC2=O)cn1] | $C_{27}H_{29}N_5O_5$ | 504 | 3-(6-(4-(6-(dimethylcarbamoyl)pyridin-3-yloxy)-3-((2-oxopyrrolidin-1-yl)methyl)phenylamino)pyridin-3-yl)propanoic acid | 505 |
| 79 | 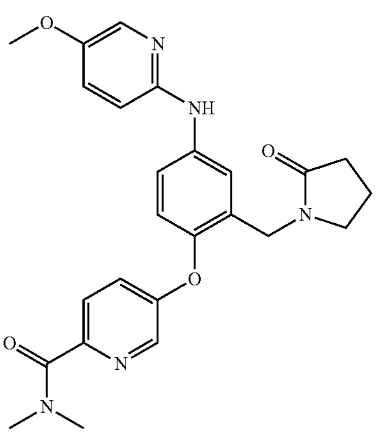 [SMILES: COc1ccc(Nc2ccc(Oc3ccc(C(=O)N(C)C)nc3)c(CN3CCCC3=O)c2)nc1] | $C_{25}H_{27}N_5O_4$ | 462 | 5-(4-(5-methoxypyridin-2-ylamino)-2-((2-oxopyrrolidin-1-yl)methyl)phenoxy)-N,N-dimethylpicolinamide | 463 |
| 80 | 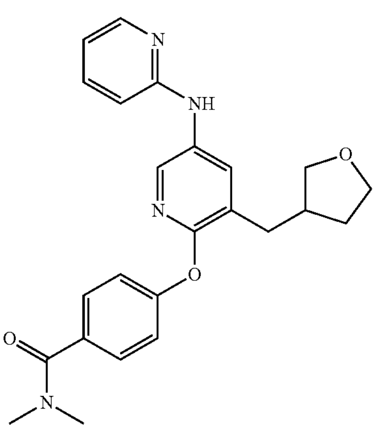 [SMILES: CN(C)C(=O)c1ccc(Oc2ncc(Nc3ccccn3)cc2CC2CCOC2)cc1] | $C_{24}H_{26}N_4O_3$ | 418 | N,N-dimethyl-4-(5-(pyridin-2-ylamino)-3-((tetrahydrofuran-3-yl)methyl)pyridin-2-yloxy)benzamide | 419 |

TABLE I-continued

| Example | Structure | Molecular Formula | Molecular Weight | Molecular Name | LC-MS [M + H](m/z) |
|---|---|---|---|---|---|
| 81 | 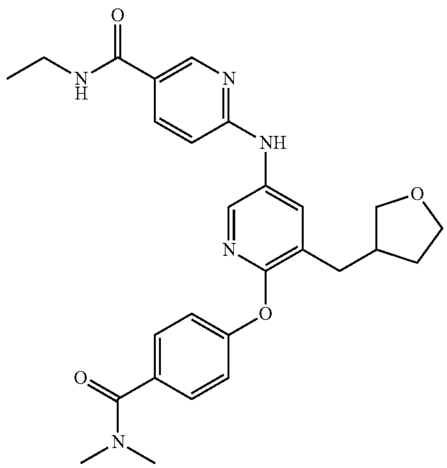 [SMILES: CCNC(=O)c1ccc(Nc2cnc(Oc3ccc(C(=O)N(C)C)cc3)c(CC3CCOC3)c2)nc1] | C₂₇H₃₁N₅O₄ | 490 | 6-(6-(4-(dimethylcarbamoyl)phenoxy)-5-((tetrahydrofuran-3-yl)methyl)pyridin-3-ylamino)-N-ethylnicotinamide | 491 |
| 82 | 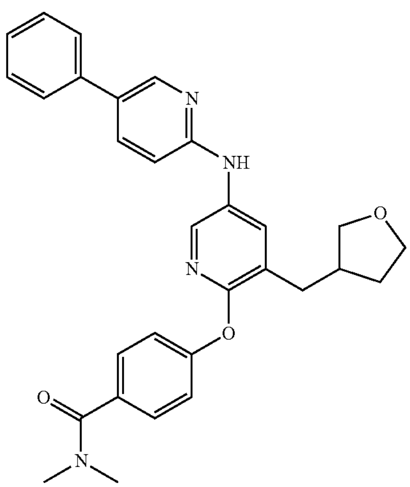 [SMILES: CN(C)C(=O)c1ccc(Oc2ncc(Nc3ccc(-c4ccccc4)cn3)cc2CC2CCOC2)cc1] | C₃₀H₃₀N₄O₃ | 495 | N,N-dimethyl-4-(5-(5-phenylpyridin-2-ylamino)-3-((tetrahydrofuran-3-yl)methyl)pyridin-2-yloxy)benzamide | 496 |
| 83 | 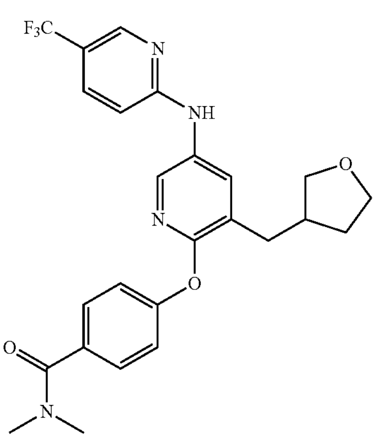 | C₂₅H₂₅F₃N₄O₃ | 486 | N,N-dimethyl-4-(3-((tetrahydrofuran-3-yl)methyl)-5-(5-(trifluoromethyl)pyridin-2-ylamino)pyridin-2-yloxy)benzamide | 487 |

TABLE I-continued

| Example | Structure | Molecular Formula | Molecular Weight | Molecular Name | LC-MS [M + H](m/z) |
|---|---|---|---|---|---|
| 84 | 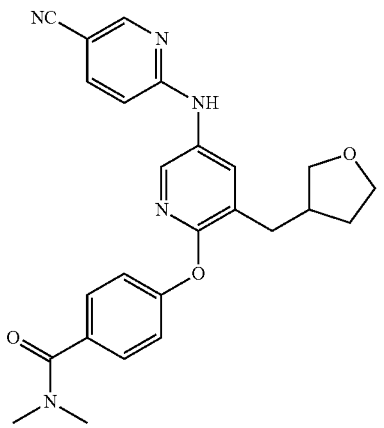 [SMILES: CN(C)C(=O)c1ccc(Oc2ncc(Nc3ccc(C#N)cn3)cc2CC2CCOC2)cc1] | C25H25N5O3 | 443 | 4-(5-(5-cyanopyridin-2-ylamino)-3-((tetrahydrofuran-3-yl)methyl)pyridin-2-yloxy)-N,N-dimethylbenzamide | 444 |
| 85 | 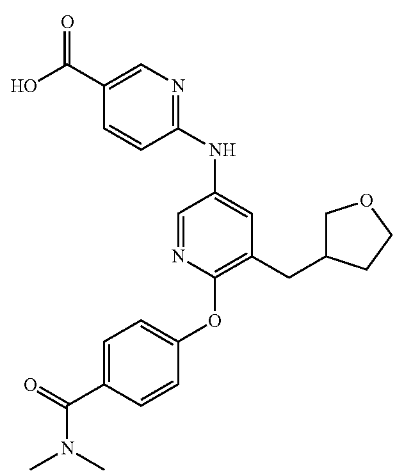 [SMILES: CN(C)C(=O)c1ccc(Oc2ncc(Nc3ccc(C(=O)O)cn3)cc2CC2CCOC2)cc1] | C25H26N4O5 | 462 | 6-(6-(4-(dimethylcarbamoyl)phenoxy)-5-((tetrahydrofuran-3-yl)methyl)pyridin-3-ylamino)nicotinic acid | 463 |
| 86 | 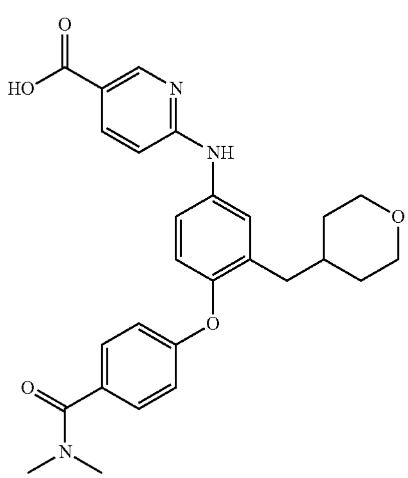 [SMILES: CN(C)C(=O)c1ccc(Oc2ccc(Nc3ccc(C(=O)O)cn3)cc2CC2CCOCC2)cc1] | C27H29N3O5 | 476 | 6-(4-(4-(dimethylcarbamoyl)phenoxy)-3-((tetrahydro-2H-pyran-4-yl)methyl)phenylamino)nicotinic acid | 477 |

TABLE I-continued

| Example | Structure | Molecular Formula | Molecular Weight | Molecular Name | LC-MS [M + H](m/z) |
|---------|-----------|-------------------|------------------|----------------|---------------------|
| 87 | 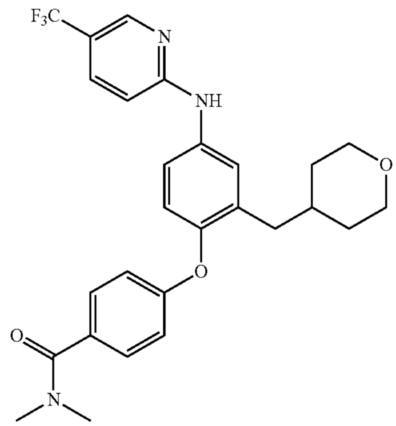 [SMILES: CN(C)C(=O)c1ccc(Oc2ccc(Nc3ccc(C(F)(F)F)cn3)cc2CC2CCOCC2)cc1] | C₂₇H₂₈F₃N₃O₃ | 500 | N,N-dimethyl-4-(2-((tetrahydro-2H-pyran-4-yl)methyl)-4-(5-(trifluoromethyl)pyridin-2-ylamino)phenoxy)benzamide | 501 |
| 88 | 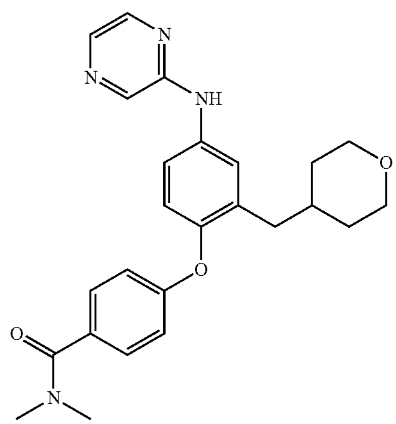 [SMILES: CN(C)C(=O)c1ccc(Oc2ccc(Nc3cnccn3)cc2CC2CCOCC2)cc1] | C₂₅H₂₈N₄O₃ | 433 | N,N-dimethyl-4-(4-(pyrazin-2-ylamino)-2-((tetrahydro-2H-pyran-4-yl)methyl)phenoxy)benzamide | 434 |
| 89 | 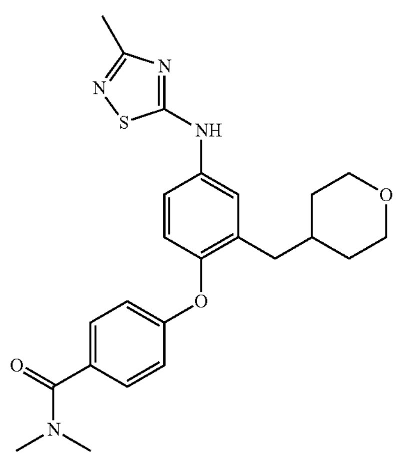 [SMILES: Cc1nsc(Nc2ccc(Oc3ccc(C(=O)N(C)C)cc3)c(CC3CCOCC3)c2)n1] | C₂₄H₂₈N₄O₃S | 453 | N,N-dimethyl-4-(4-(3-methyl-1,2,4-thiadiazol-5-ylamino)-2-((tetrahydro-2H-pyran-4-yl)methyl)phenoxy)benzamide | 454 |

TABLE I-continued

| Example | Structure | Molecular Formula | Molecular Weight | Molecular Name | LC-MS [M + H](m/z) |
|---------|-----------|-------------------|------------------|----------------|---------------------|
| 90 | 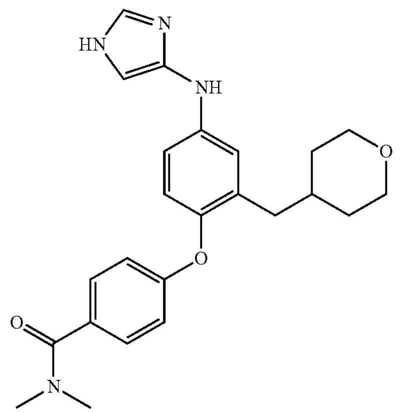 [SMILES: CN(C)C(=O)c1ccc(Oc2ccc(Nc3c[nH]cn3)cc2CC2CCOCC2)cc1] | C₂₄H₂₈N₄O₃ | 421 | 4-(4-(1H-imidazol-4-yl amino)-2-((tetrahydro-2H-pyran-4-yl)methyl) phenoxy)-N,N-dimethylbenzamide | 422 |
| 91 | 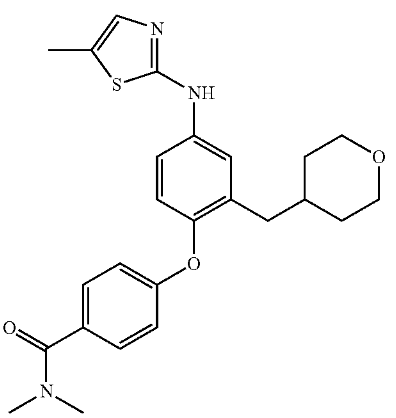 [SMILES: Cc1cnc(Nc2ccc(Oc3ccc(C(=O)N(C)C)cc3)c(CC3CCOCC3)c2)s1] | C₂₅H₂₉N₃O₃S | 452 | N,N-dimethyl-4-(4-(5-methylthiazol-2-ylamino)-2-((tetrahydro-2H-pyran-4-yl)methyl) phenoxy)benzamide | 453 |
| 92 | 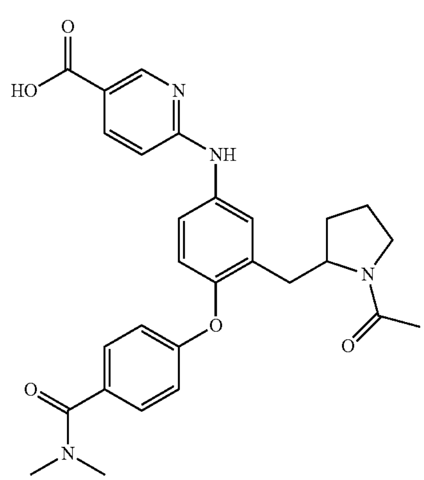 [SMILES: CC(=O)N1CCCC1Cc1cc(Nc2ccc(C(=O)O)cn2)ccc1Oc1ccc(C(=O)N(C)C)cc1] | C₂₈H₃₀N₄O₅ | 503 | 6-(3-((1-acetylpyrrolidin-2-yl)methyl)-4-(4-(dimethylcarbamoyl) phenoxy) phenylamino) nicotinic acid | 504 |

TABLE I-continued

| Example | Structure | Molecular Formula | Molecular Weight | Molecular Name | LC-MS [M + H](m/z) |
|---|---|---|---|---|---|
| 93 | 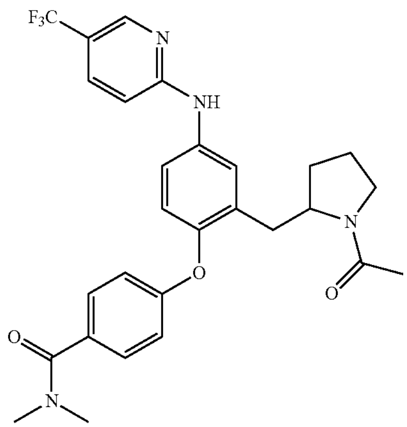 [SMILES: CC(=O)N1CCCC1Cc1cc(Nc2ccc(C(F)(F)F)cn2)ccc1Oc1ccc(C(=O)N(C)C)cc1] | C₂₈H₂₉F₃N₄O₃ | 527 | 4-(2-((1-acetylpyrrolidin-2-yl)methyl)-4-(5-(trifluoromethyl)pyridin-2-ylamino)phenoxy)-N,N-dimethylbenzamide | 528 |
| 94 | 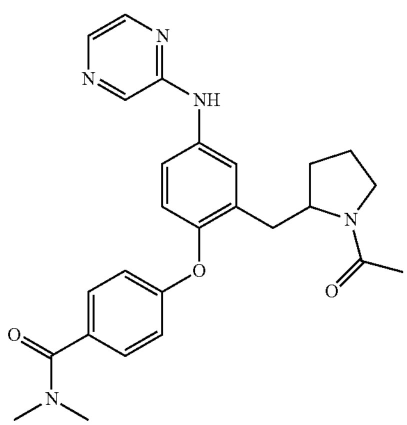 [SMILES: CC(=O)N1CCCC1Cc1cc(Nc2cnccn2)ccc1Oc1ccc(C(=O)N(C)C)cc1] | C₂₆H₂₉N₅O₃ | 460 | 4-(2-((1-acetylpyrrolidin-2-yl)methyl)-4-(pyrazin-2-ylamino)phenoxy)-N,N-dimethylbenzamide | 461 |
| 95 | 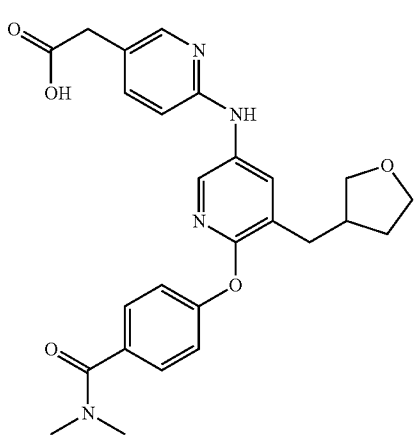 [SMILES: CN(C)C(=O)c1ccc(Oc2ncc(Nc3ccc(CC(=O)O)cn3)cc2CC2CCOC2)cc1] | C₂₆H₂₈N₄O₅ | 477 | 2-(6-(6-(4-(dimethylcarbamoyl)phenoxy)-5-((tetrahydrofuran-3-yl)methyl)pyridin-3-ylamino)pyridin-3-yl)acetic acid | 478 |

TABLE I-continued

| Example | Structure | Molecular Formula | Molecular Weight | Molecular Name | LC-MS [M + H](m/z) |
|---|---|---|---|---|---|
| 96 | 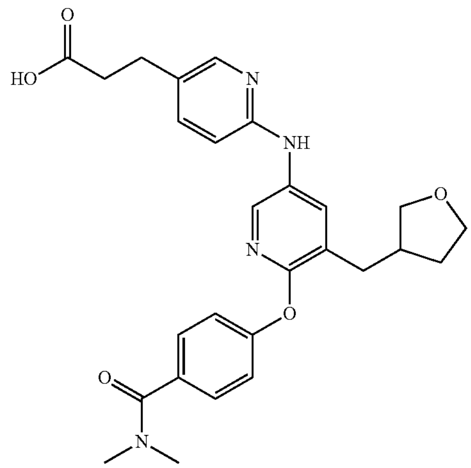 [SMILES: CN(C)C(=O)c1ccc(Oc2ncc(Nc3ccc(CCC(=O)O)cn3)cc2CC2CCOC2)cc1] | $C_{27}H_{30}N_4O_5$ | 491 | 3-(6-(6-(4-(dimethylcarbamoyl)phenoxy)-5-((tetrahydrofuran-3-yl)methyl)pyridin-3-ylamino)pyridin-3-yl)propanoic acid | 492 |
| 97 | 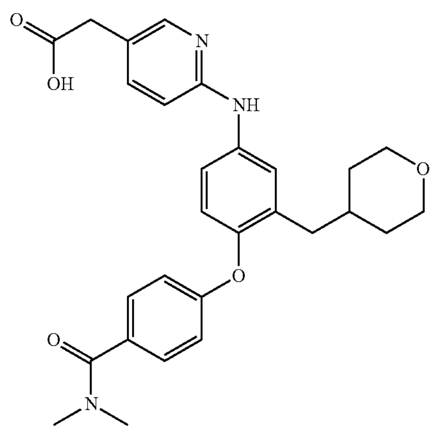 [SMILES: CN(C)C(=O)c1ccc(Oc2ccc(Nc3ccc(CC(=O)O)cn3)cc2CC2CCOCC2)cc1] | $C_{28}H_{31}N_3O_5$ | 490 | 2-(6-(4-(4-(dimethylcarbamoyl)phenoxy)-3-((tetrahydro-2H-pyran-4-yl)methyl)phenylamino)pyridin-3-yl)acetic acid | 491 |
| 98 | 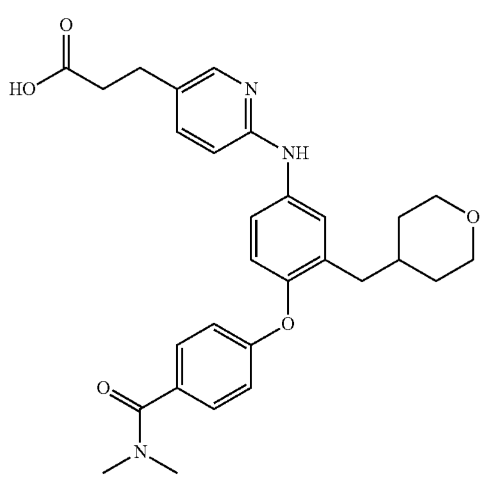 [SMILES: CN(C)C(=O)c1ccc(Oc2ccc(Nc3ccc(CCC(=O)O)cn3)cc2CC2CCOCC2)cc1] | $C_{29}H_{33}N_3O_5$ | 504 | 3-(6-(4-(4-(dimethylcarbamoyl)phenoxy)-3-((tetrahydro-2H-pyran-4-yl)methyl)phenylamino)pyridin-3-yl)propanoic acid | 505 |

TABLE I-continued

| Example | Structure | Molecular Formula | Molecular Weight | Molecular Name | LC-MS [M + H](m/z) |
|---|---|---|---|---|---|
| 99 | 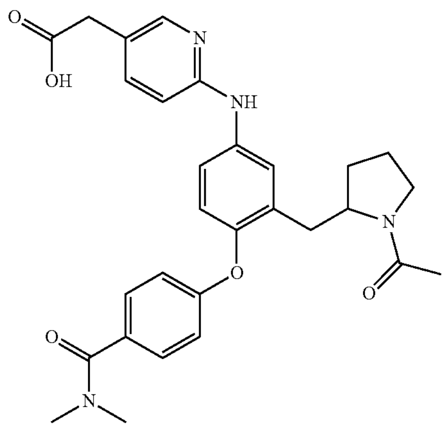 [SMILES: CC(=O)N1CCCC1Cc1cc(Nc2ccc(CC(=O)O)cn2)ccc1Oc1ccc(C(=O)N(C)C)cc1] | $C_{29}H_{32}N_4O_5$ | 517 | 2-(6-(3-((1-acetylpyrrolidin-2-yl)methyl)-4-(4-(dimethylcarbamoyl)phenoxy)phenylamino)pyridin-3-yl)acetic acid | 518 |
| 100 | 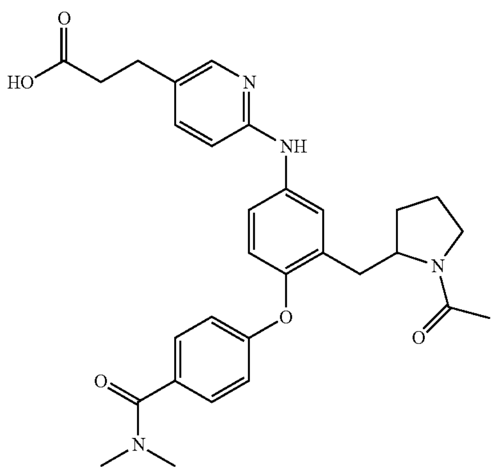 [SMILES: CC(=O)N1CCCC1Cc1cc(Nc2ccc(CCC(=O)O)cn2)ccc1Oc1ccc(C(=O)N(C)C)cc1] | $C_{30}H_{34}N_4O_5$ | 531 | 3-(6-(3-((1-acetylpyrrolidin-2-yl)methyl)-4-(4-(dimethylcarbamoyl)phenoxy)phenylamino)pyridin-3-yl)propanoic acid | 532 |
| 101 | 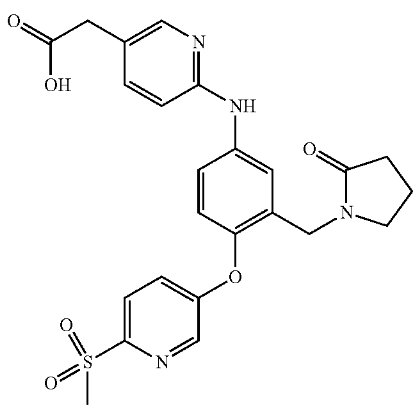 [SMILES: CS(=O)(=O)c1ccc(Oc2ccc(Nc3ccc(CC(=O)O)cn3)cc2CN2CCCC2=O)cn1] | $C_{24}H_{24}N_4O_6S$ | 497 | 2-(6-(4-(6-(methylsulfonyl)pyridin-3-yloxy)-3-((2-oxopyrrolidin-1-yl)methyl)phenylamino)pyridin-3-yl)acetic acid | 498 |

TABLE I-continued

| Example | Structure | Molecular Formula | Molecular Weight | Molecular Name | LC-MS [M + H](m/z) |
|---|---|---|---|---|---|
| 102 | 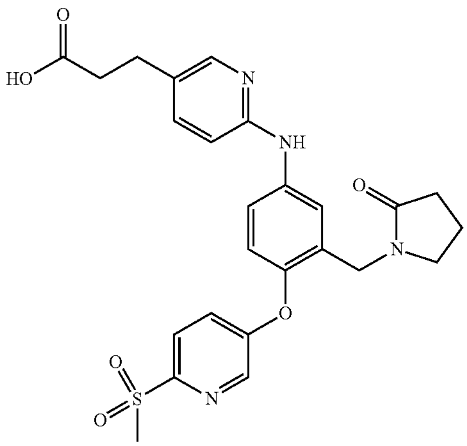 [SMILES: CS(=O)(=O)c1ccc(Oc2ccc(Nc3ccc(CCC(=O)O)cn3)cc2CN2CCCC2=O)cn1] | C$_{25}$H$_{26}$N$_4$O$_6$S | 497 | 3-(6-(4-(6-(methylsulfonyl) pyridin-3-yloxy)-3-((2-oxopyrrolidin-1-yl) methyl)phenylamino) pyridin-3-yl)propanoic acid | 498 |
| 103 | 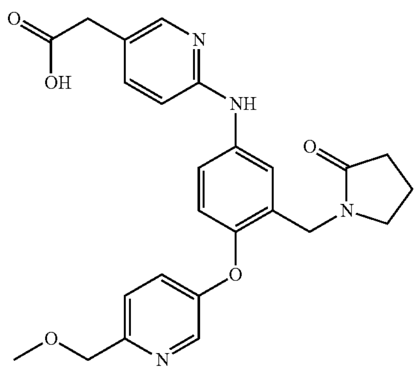 [SMILES: COCc1ccc(Oc2ccc(Nc3ccc(CC(=O)O)cn3)cc2CN2CCCC2=O)cn1] | C$_{25}$H$_{26}$N$_4$O$_5$ | 462 | 2-(6-(4-(6-(methoxymethyl) pyridin-3-yloxy)-3-((2-oxopyrrolidin-1-yl) methyl)phenylamino) pyridin-3-yl)acetic acid | 463 |
| 104 | 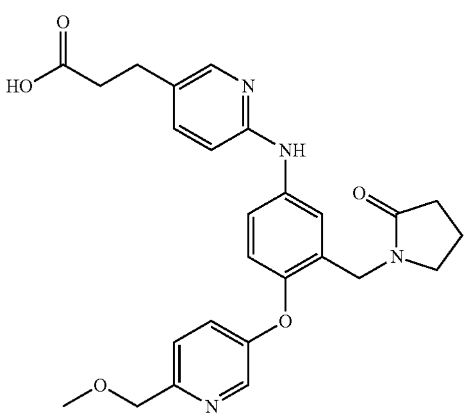 [SMILES: COCc1ccc(Oc2ccc(Nc3ccc(CCC(=O)O)cn3)cc2CN2CCCC2=O)cn1] | C$_{26}$H$_{28}$N$_4$O$_5$ | 477 | 3-(6-(4-(6-(methoxymethyl) pyridin-3-yloxy)-3-((2-oxopyrrolidin-1-yl) methyl)phenylamino) pyridin-3-yl)propanoic acid | 478 |

Example A

Glucokinase Activation Assay

The final assay volume was 200 uL and the final buffer conditions used in this assay were as follows: 25 mM HEPES, 5 mM glucose, 1 mM ATP, 2 mM MgCl2, 1 mM NAD, 1 mM DTT, 8.5 U/mL G6PDH, 100 nM glucokinase, and 25 mM KCl. The buffer pH was 7.1. The mixture A was first made containing KCl, MgCl2, DTT and Glucose in HEPES buffer. The mixture B was made containing NAD and ATP. The test compound in DMSO solution, the mixture A, the mixture B and G6PDH were first mixed in a 96-well plate. Glucokinase was then added to initiate the reaction, and the absorbance at 340 nm was monitored every 5 mins. The activity of glucokinase was represented by the initial generation rate of glucose-6-phosphate, which was calculated by drawing the slope values from the absorbance changing curve at 340 nm vs. the time points. Compounds of this invention have an EC50 value as measured using the assay described herein of less than 50 μM. Compounds preferably have an EC50 in the range of 10 nM to 10 μM, more preferably in the range of 10 nM to 1 μM, The activity test results of some examples of the present invention are shown in Table II.

TABLE II

| Example | EC50, Glucokinase Activation (μM) |
| --- | --- |
| Example 6 | 2 |
| Example 13 | 2 |
| Example 65 | 5 |
| Example 78 | 1.5 |

Example B

Glucose Tolerance Test

Mice were grouped based on fasting glucose levels, and then was orally given 30 mg/kg of test compounds. After 1 hr., the blood glucose levels were measured, and then a glucose dose of 2 g/kg was given, and the blood glucose levels were monitored at 30 mins., 60 mins. and 120 mins. The glucose levels vs. the time points were drawn to show the glucose tolerance capabilities. The test results of some examples of the present invention are shown in FIG. 1.

Although the present invention has been described in considerable detail with reference to certain preferred versions thereof, other versions are possible. Therefore, the spirit and scope of the present invention should not be limited to the description of the preferred versions described herein. All features disclosed in the specification, including the abstract and drawings, and all the steps in any method or process disclosed, may be combined in any combination, except combinations where at least some of such features and/or steps are mutually exclusive. Each feature disclosed in the specification, including abstract and drawings, can be replaced by alternative features serving the same, equivalent or similar purpose, unless expressly stated otherwise. Thus, unless expressly stated otherwise, each feature disclosed is one example only of a generic series of equivalent or similar features. Various modifications of the invention, in addition to those described herein, will be apparent to those skilled in the art from the foregoing description. Such modifications are also intended to fall within the scope of the appended claims. Each reference cited in the present application is herein incorporated by reference in its entirety.

The invention claimed is:

1. A compound of Formula (I), or pharmaceutically acceptable salts thereof,

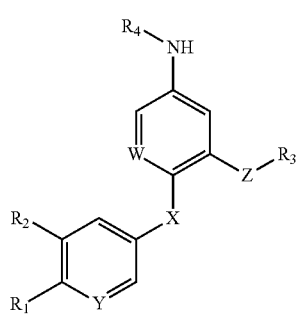

Formula (I)

wherein:
W and Y are each C;
X is O;
Z is C;

$R_1$ is selected from the group consisting of —H, alkanyl, substituted alkanyl, alkenyl, substituted alkenyl, alkynyl, substituted alkynyl, alkoxy, substituted alkoxy, C(=O)$R_5$, S$R_5$, SO$_2$$R_5$ and haloalkyl; $R_5$ is selected from the group consisting of $C_{1-6}$ alkanyl, substituted $C_{1-6}$ alkanyl, alkoxy, substituted alkoxy and N$R_6$$R_7$; $R_6$ and $R_7$ are independently selected from the group consisting of —H, $C_{1-6}$ alkanyl, and substituted $C_{1-6}$ alkanyl, or $R_6$ and $R_7$ can join together to form a 3 to 6 membered ring or a substituted 3 to 6 membered ring;

$R_2$ is selected from the group consisting of —H, alkanyl, substituted alkanyl, halogen and haloalkyl;

$R_3$ is selected from the group consisting of substituted alkanyl, alkenyl, substituted alkenyl, alkynyl, substituted alkynyl, cycloalkyl, substituted cycloalkyl, heterocycloalkyl and substituted heterocycloalkyl; and $R_4$ is selected from the group consisting of heteroaryl and substituted heteroaryl, wherein at least one ortho atom of the heteroaryl connected with NH in Formula (I) is N.

2. The compound of claim 1, wherein $R_1$ is selected from the group consisting of C(=O)$R_5$, S$R_5$, SO$_2$$R_5$ and haloalkyl; and wherein $R_5$ is selected the group consisting of $C_{1-3}$alkanyl, substituted $C_{1-3}$alkanyl, N$R_6$$R_7$, $C_{1-6}$alkoxy, and substituted $C_{1-6}$alkoxy.

3. The compound of claim 1, wherein $R_2$ is —H; wherein $R_3$ is selected from the group consisting of cycloalkanyl, substituted cycloalkanyl, heterocycloalkyl and substituted heterocycloalkyl; and wherein $R_4$ is substituted 5- or 6-membered heteroaryl.

4. The compound of claim 2, wherein $R_3$ is

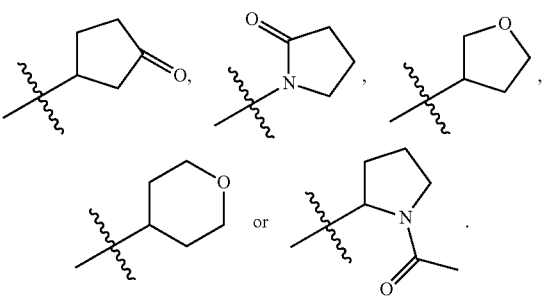

5. The compound of claim 3, wherein $R_1$ is SO$_2$$R_5$; $R_5$ is $C_{1-3}$alkanyl.

6. The compound of claim 1, wherein $R_3$ is

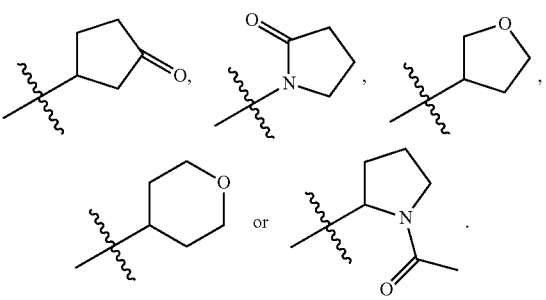

7. The compound of claim 1, wherein the compound is selected from the group consisting of:
ethyl 6-(4-(4-(4-(methylsulfonyl)phenoxy)-3-((3-oxocyclopentyl)methyl)phenylamino) nicotinate;

3-(2-(4-(methylsulfonyl)phenoxy)-5-(5-methylthiazol-2-ylamino)benzyl)cyclopentanone;
3-(2-(4-(methylsulfonyl)phenoxy)-5-(pyrazin-2-ylamino) benzyl)cyclopentanone;
3-(5-(3-methyl-1,2,4-thiadiazol-5-ylamino)-2-(4-(methylsulfonyl) phenoxy)benzyl)cyclopentanone;
3-(5-(1H-imidazol-4-ylamino)-2-(4-(methylsulfonyl)phenoxy)benzyl)cyclopentanone;
3-(2-(4-(methylsulfonyl)phenoxy)-5-(5-(trifluoromethyl) pyridin-2-ylamino)benzyl)cyclopentanone;
ethyl 6-(4-(4-(methylsulfonyl)phenoxy)-3-((tetrahydro-2H-pyran-4-yl)methyl)phenylamino)nicotinate;
N-(4-(4-(methylsulfonyl)phenoxy)-3-((tetrahydro-2H-pyran-4-yl)methyl)phenyl)-5-(trifluoromethyl)pyridin-2-amine;
N-(4-(4-(methylsulfonyl)phenoxy)-3-((tetrahydro-2H-pyran-4-yl)methyl)phenyl) pyrazin-2-amine;
3-methyl-N-(4-(4-(methylsulfonyl)phenoxy)-3-((tetrahydro-2H-pyran-4-yl)methyl)phenyl)-1,2,4-thiadiazol-5-amine;
N-(4-(4-(methylsulfonyl)phenoxy)-3-((tetrahydro-2H-pyran-4-yl)methyl)phenyl)-1H-imidazol-4-amine;
5-methyl-N-(4-(4-(methylsulfonyl)phenoxy)-3-((tetrahydro-2H-pyran-4-yl)methyl)phenyl)thiazol-2-amine;
ethyl 6-(3-((1-acetylpyrrolidin-2-yl)methyl)-4-(4-(methylsulfonyl) phenoxy)phenylamino)nicotinate;
1-(2-(2-(4-(methylsulfonyl)phenoxy)-5-(5-(trifluoromethyl)pyridin-2-ylamino)benzyl) pyrrolidin-1-yl)ethanone;
1-(2-(2-(4-(methylsulfonyl)phenoxy)-5-(pyrazin-2-ylamino)benzyl)pyrrolidin-1-yl) ethanone;
1-(2-(5-(3-methyl-1,2,4-thiadiazol-5-ylamino)-2-(4-(methylsulfonyl) phenoxy)benzyl) pyrrolidin-1-yl)ethanone;
1-(2-(5-(1H-imidazol-4-ylamino)-2-(4-(methylsulfonyl) phenoxy)benzyl)pyrrolidin-1-yl)ethanone;
1-(2-(2-(4-(methylsulfonyl)phenoxy)-5-(5-methylthiazol-2-ylamino)benzyl)pyrrolidin-1-yl)ethanone;
ethyl 6-(4-(4-dimethylcarbamoyl)phenoxy)-3-((3-oxocyclopentyl)methyl)phenylamino)nicotinate;
N,N-dimethyl-4-(4-(5-methylthiazol-2-ylamino)-2-((3-oxocyclopentyl)methylphenoxy)benzamide;
N,N-dimethyl-4-(2-((3-oxocyclopentyl)methyl)-4-(pyrazin-2-ylamino) phenoxy)benzamide;
N,N-dimethyl-4-(4-(3-methyl-1,2,4-thiadiazol-5-ylamino)-2-((3-oxocyclopentyl)methyl)phenoxy)benzamide;
4-(4-(1H-imidazol-4-ylamino)-2-((3-oxocyclopentyl)methyl)phenoxy)-N,N-dimethylbenzamide;
N,N-dimethyl-4-(2-((3-oxocyclopentyl)methyl)-4-(5-(trifluoromethyl)pyridin-2-ylamino)phenoxy)benzamide;
6-(4-(4-(dimethylcarbamoyl)phenoxy)-3-((tetrahydro-2H-pyran-4-yl)methyl)phenyl amino)nicotinic acid;
N,N-dimethyl-4-(2-((tetrahydro-2H-pyran-4-yl)methyl)-4-(5-(trifluoromethyl)pyridin-2-ylamino)phenoxy)benzamide;
N,N-dimethyl-4-(4-(pyrazin-2-ylamino)-2-((tetrahydro-2H-pyran-4-yl)methyl) phenoxy)benzamide;
N,N-dimethyl-4-(4-(3-methyl-1,2,4-thiadiazol-5-ylamino)-2-((tetrahydro-2H-pyran-4-yl)methyl)phenoxy)benzamide;
4-(4-(1H-imidazol-4-ylamino)-2-((tetrahydro-2H-pyran-4-yl)methyl)phenoxy)-N,N-dimethylbenzamide;
N,N-dimethyl-4-(4-(5-methylthiazol-2-ylamino)-2-((tetrahydro-2H-pyran-4-yl)methyl) phenoxy)benzamide;
6-(3-((1-acetylpyrrolidin-2-yl)methyl)-4-(4-(dimethylcarbamoyl) phenoxy)phenyl amino)nicotinic acid;
4-(2-((1-acetylpyrrolidin-2-yl)methyl)-4-(5-(trifluoromethyl)pyridin-2-ylamino) phenoxy)-N,N-dimethylbenzamide;
4-(2-((1-acetylpyrrolidin-2-yl)methyl)-4-(pyrazin-2-ylamino)phenoxy)-N,N-dimethylbenzamide;
2-(6-(4-(4-(dimethylcarbamoyl)phenoxy) 3-((tetrahydro-2H-pyran-4-yl)methyl)phenylamino)pyridin-3-yl) acetic acid;
3-(6-(4-(4-(dimethylcarbamoyl)phenoxy)-3-((tetrahydro-2H-pyran-4-yl)methyl)phenylamino)pyridin-3-yl)propanoic acid;
2-(6-(3-((1-acetylpyrrolidin-2-yl)methyl)-4-(4-(dimethylcarbamoyl) phenoxy)phenylamino)pyridin-3-yl)acetic acid; or
3-(6-(3-((1-acetylpyrrolidin-2-yl)methyl)-4-(4-(dimethylcarbamoyl)phenoxy)phenylamino)pyridin-3-yl)propanoic acid.

8. A method of modulating glucokinase levels or activities in animals or humans by administering to the subject at least one compound of claim 1.

9. A method for treating and/or preventing type II diabetes or related disease thereof, by administering to the subject a therapeutically effective amount of the compound of claim 1.

10. A method for treating and/or preventing type I diabetes or related disease thereof, by administering to the subject a therapeutically effective amount of the compound of claim 1.

11. A method for treating and/or preventing obesity or related disease thereof, by administering to the subject a therapeutically effective amount of the compound of claim 1.

12. The compound of claim 5, wherein $R_4$ is substituted 5 or 6 membered heteroaryl, and wherein one substitution is $C_{1-3}$ carboxylate.

13. The compound of claim 6, wherein $R_4$ is selected from the group consisting of 5-membered heteroaryl, 6-membered heteroaryl, substituted 5-heteroaryl and 6-membered heteroaryl.

14. The compound of claim 13, wherein $R_4$ is selected from the group consisting of

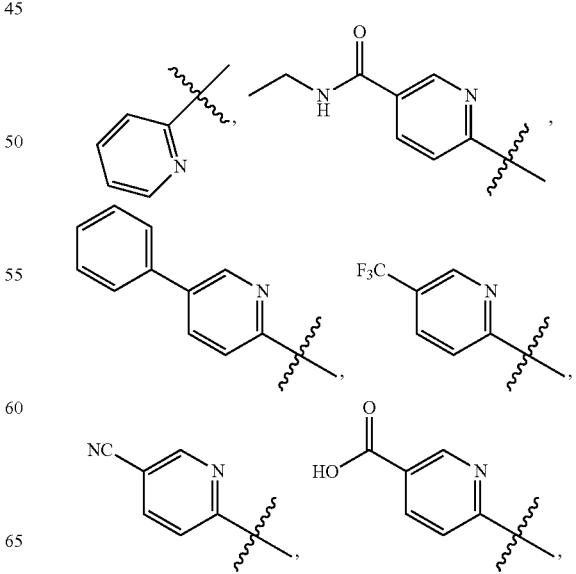

-continued

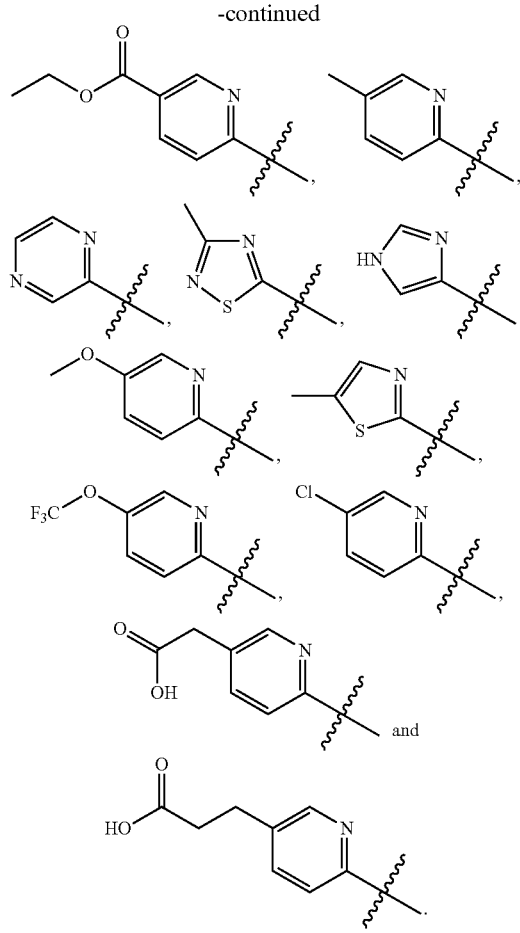

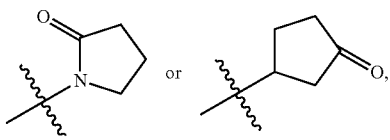 [SMILES: *N1CCCC1=O ; "or" ; *C1CCC(=O)C1]

and wherein R₄ is selected from the group consisting of

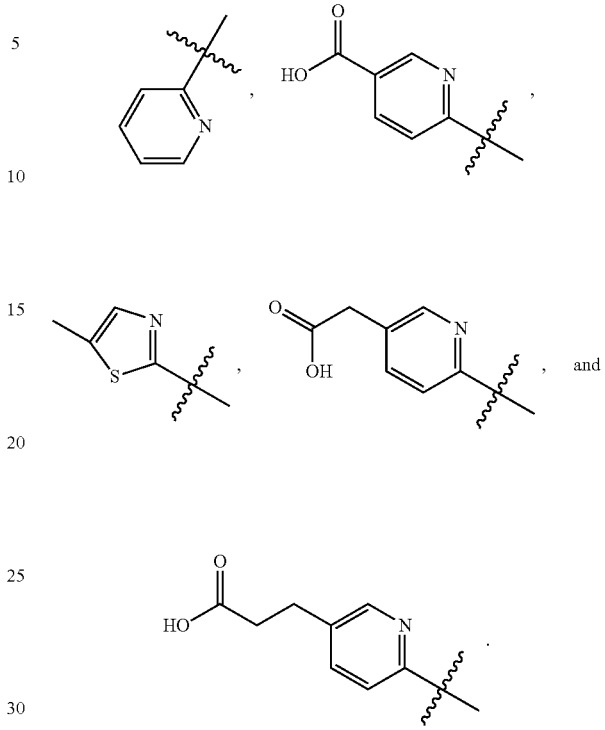

15. The compound of claim 14, wherein R is selected from the group consisting of lower alkanyl, $C_{1-6}$alkoxy, $C(=O)R_5$ and $SO_2R_5$, wherein $R_5$ is selected from the group consisting of lower alkanyl and $NR_6R_7$, and wherein $R_6$ and $R_7$ are independently selected from the group consisting of —H and lower alkanyl, or $R_6$ and $R_7$ can join together to form a 3 to 6 membered ring.

16. The compound of claim 15, wherein $R_2$ is —H, or halogen.

17. The compound of claim 16, wherein $R_3$ is

18. The compound of claim 16, wherein R is —H; wherein $R_1$ is $C(=O)NR_6R_7$ or $SO_2R_5$; and wherein $R_5$ is $C_{1-3}$alkanyl.

19. A pharmaceutical composition, comprising a therapeutically effective amount of at least one compound of claim 1, and at least one pharmaceutically acceptable excipient, adjuvant or carrier.

20. A pharmaceutical composition, comprising a therapeutically effective amount of at least one compound of claim 7, and at least one pharmaceutically acceptable excipient, adjuvant or carrier.

21. A method of modulating glucokinase levels or activities in animals or humans by administering to the subject at least one compound of claim 7.

22. A method for treating and/or preventing type II diabetes or related disease thereof, by administering to the subject a therapeutically effective amount of the compound of claim 7.

23. A method for treating and/or preventing type I diabetes or related disease thereof, by administering to the subject a therapeutically effective amount of the compound of claim 7.

24. A method for treating and/or preventing obesity or related disease thereof, by administering to the subject a therapeutically effective amount of the compound of claim 7.

* * * * *